(12) United States Patent
Mitsunaga

(10) Patent No.: US 10,888,216 B2
(45) Date of Patent: Jan. 12, 2021

(54) ENDOSCOPE DEVICE, ENDOSCOPE SYSTEM AND INSPECTION METHOD

(71) Applicant: Olympus Corporation, Hachioji (JP)

(72) Inventor: Osamu Mitsunaga, Kokubunji (JP)

(73) Assignee: OLYMPUS CORPORATION, Tokyo (JP)

(*) Notice: Subject to any disclaimer, the term of this patent is extended or adjusted under 35 U.S.C. 154(b) by 118 days.

(21) Appl. No.: 16/130,270

(22) Filed: Sep. 13, 2018

(65) Prior Publication Data

US 2019/0082943 A1 Mar. 21, 2019

(30) Foreign Application Priority Data

Sep. 20, 2017 (JP) ................................ 2017-180448

(51) Int. Cl.
| | | |
|---|---|---|
| *G06K 9/00* | (2006.01) | |
| *A61B 1/05* | (2006.01) | |
| *A61B 1/00* | (2006.01) | |
| *G02B 23/24* | (2006.01) | |
| *A61B 1/06* | (2006.01) | |

(52) U.S. Cl.
CPC .............. *A61B 1/05* (2013.01); *A61B 1/0005* (2013.01); *A61B 1/00006* (2013.01); *A61B 1/00009* (2013.01); *A61B 1/00055* (2013.01); *A61B 1/00096* (2013.01); *A61B 1/00163* (2013.01); *G02B 23/2407* (2013.01); *A61B 1/0684* (2013.01)

(58) Field of Classification Search
CPC ..... A61B 1/05; A61B 1/0005; A61B 1/00055; A61B 1/00009; A61B 1/00006; A61B 1/00163; A61B 1/00096; A61B 1/0684; G02B 23/2407

USPC ......................................................... 382/128
See application file for complete search history.

(56) References Cited

U.S. PATENT DOCUMENTS

| | | | | |
|---|---|---|---|---|
| 2006/0078193 | A1* | 4/2006 | Brummel | G01N 21/8806 382/152 |
| 2012/0221569 | A1* | 8/2012 | Sato | G06F 16/51 707/736 |
| 2012/0297600 | A1* | 11/2012 | Ullrich | G01N 21/9515 29/407.04 |
| 2013/0345502 | A1* | 12/2013 | Mitsunaga | G11B 27/105 600/103 |
| 2014/0046941 | A1* | 2/2014 | Sato | G16H 15/00 707/736 |
| 2015/0035969 | A1* | 2/2015 | Kobayashi | F01D 25/285 348/82 |
| 2015/0168263 | A1* | 6/2015 | Mueller | G01N 21/954 348/82 |

(Continued)

FOREIGN PATENT DOCUMENTS

JP 2008225012 9/2008

*Primary Examiner* — Van D Huynh
(74) *Attorney, Agent, or Firm* — Scully, Scott, Murphy & Presser, P.C.

(57) ABSTRACT

An endoscope device includes an imaging unit and an operation unit that is configured to receive results of an assessment on an endoscopic image of an object as captured by the imaging unit. A retrieval control unit is configured to retrieve one of assessment assist images stored in a data accumulation unit based on information on the assessment results. A display control unit is configured to display the retrieved one assessment assist image along with the endoscopic image on a display unit.

15 Claims, 11 Drawing Sheets

(56) References Cited

U.S. PATENT DOCUMENTS

2018/0211385 A1* 7/2018 Imai ................... A61B 1/00
2020/0253673 A1* 8/2020 Azizian ............... A61B 34/32

* cited by examiner

FIG. 3

```
root
  ├── ¥DCIM¥IV70001¥IV~~~001.jpg
  │              ¥IV~~~002.jpg
  │              ¥IV~~~003.jpg
  │                  ⋮
  ├── ¥ENGINE1_SN001¥HPC_STAGE1_ZONE1_1¥ENGINE1_SN001_HPC_STAGE1_ZONE1_1_A_001.jpg
  │       │                            ¥ENGINE1_SN001_HPC_STAGE1_ZONE1_1_A_002.jpg
  │       │                                  ⋮
  │       ├── ¥HPC_STAGE1_ZONE1_2¥ENGINE1_SN001_HPC_STAGE1_ZONE1_2_D_001.jpg
  │       │                      ¥ENGINE1_SN001_HPC_STAGE1_ZONE1_2_C_002.jpg
  │       │                            ⋮
  │       ├── ¥HPC_STAGE1_ZONE2_1¥ENGINE1_SN001_HPC_STAGE1_ZONE2_1_B_001.jpg
  │                              ¥ENGINE1_SN001_HPC_STAGE1_ZONE2_1_B_002.jpg
  │                                    ⋮
  ├── ¥ENGINE2_SN002¥HPC_STAGE1_ZONE1_1¥ENGINE2_SN002_HPC_STAGE1_ZONE1_1_A_001.jpg
  │       │                            ¥ENGINE2_SN002_HPC_STAGE1_ZONE1_1_A_002.jpg
  │       │                                  ⋮
  │       ├── ¥HPC_STAGE1_ZONE1_3¥ENGINE2_SN002_HPC_STAGE1_ZONE1_3_A_001.jpg
  │                              ¥ENGINE2_SN002_HPC_STAGE1_ZONE1_3_A_002.jpg
                                         ⋮
```

ENDOSCOPE DEVICE, ENDOSCOPE SYSTEM AND INSPECTION METHOD

CROSS-REFERENCE TO RELATED APPLICATION

This application claims priority to Japanese Patent Application JP 2017-180448 filed in the Japan Patent Office on Sep. 20, 2017, the content of which is hereby incorporated by reference in its entirety.

TECHNICAL FIELD

The disclosed technology relates to an endoscope device, an endoscope system and an inspection method.

DESCRIPTION OF THE RELATED ART

Conventionally, endoscope devices have been widely used in the industrial and medical fields. An endoscope device or system has an insert section with an imaging unit arranged in a tip portion thereof. A user can bring the tip portion of the insert section close to an object. The endoscope system would then display on a monitor an image captured by the imaging unit arranged in the tip portion of the insert section. The endoscope system can record the image in a storage device as needed. For example, the user can connect a storage device such as a USB memory to a device console and can record endoscopic images in the storage device. In Japanese Patent Laid-Open No. 2008-225012, for example, discloses a technology that records a past image of every turbine blade.

Known endoscope devices include those which are configured to enable further inspection results of an image file upon recording an endoscopic image acquired by an inspection. The inspection results are such as, for example, the kind and rank of damage. The use of these endoscopic image and information on inspection results enables effective preparation of an inspection report.

BRIEF SUMMARY OF EMBODIMENTS

One aspect of the disclosed technology herein is directed to an endoscope device having an imaging unit and an operation unit that is configured to receive results of an assessment on an endoscopic image of an object as captured by the imaging unit. A retrieval control unit is configured to retrieve one of assessment assist images stored in a data accumulation unit based on information on the assessment results. A display control unit is configured to display the retrieved one assessment assist image along with the endoscopic image on a display unit.

Another aspect of the disclosed technology herein is directed to an endoscope system having an endoscope device. The endoscope device has an imaging unit and an operation unit that is configured to receive results of an assessment on an endoscopic image of an object as captured by the imaging unit. A retrieval control unit is configured to retrieve one of assessment assist images stored in a data accumulation unit based on information on the assessment results. A display control unit is configured to display the retrieved one assessment assist image along with the endoscopic image on a display unit. A server is connected to the endoscope device via a network and the data accumulation unit is included in the server.

A further aspect of the disclosed technology herein is directed to an inspection method for receiving results of an assessment on an endoscopic image acquired. Next, retrieving one of assessment assist images based on information on the assessment results. Finally, displaying the retrieved one assessment image along with the endoscopic image.

BRIEF DESCRIPTION OF THE DRAWINGS

The technology disclosed herein, in accordance with one or more various embodiments, is described in detail with reference to the following figures. The drawings are provided for purposes of illustration only and merely depict typical or example embodiments of the disclosed technology. These drawings are provided to facilitate the reader's understanding of the disclosed technology and shall not be considered limiting of the breadth, scope, or applicability thereof. It should be noted that for clarity and ease of illustration these drawings are not necessarily made to scale.

FIG. 3 is an illustration of examples of folders having a hierarchical structure executed by the endoscope device of FIG. 1;

DETAILED DESCRIPTION OF THE EMBODIMENTS

In the following description, various embodiments of the technology will be described. For purposes of explanation, specific configurations and details are set forth in order to provide a thorough understanding of the embodiments. However, it will also be apparent to one skilled in the art that the technology disclosed herein may be practiced without the specific details. Furthermore, well-known features may be omitted or simplified in order not to obscure the embodiment being described.

An endoscope device according to one aspect of the disclosed technology includes an imaging unit, an operation unit, a retrieval control unit, and a display control unit. The operation unit is configured to receive results of an assessment of an endoscopic image corresponding to an inspected object captured by the imaging unit. The retrieval control unit is configured to retrieve one of assessment assist images stored in a data accumulation unit based on the information derived from the results of the assessment. The display control unit is configured to display the one of assessment assist images along with the endoscopic image on a display unit.

An endoscope system according to another aspect of the disclosed technology includes the endoscope device according to the one aspect of the disclosed technology, and a server connected with the endoscope device via a network. The data accumulation unit is included in the server.

An inspection method according to a further aspect of the disclosed technology includes receiving results of an assessment on an endoscopic image acquired by an imaging unit, retrieving one of assessment assist images, which are stored in a data accumulation unit, by a retrieval control unit based on information on the assessment results, and displaying by using a display control unit, the one of assessment assist images along with the endoscopic image on a display unit.

Figure 1:
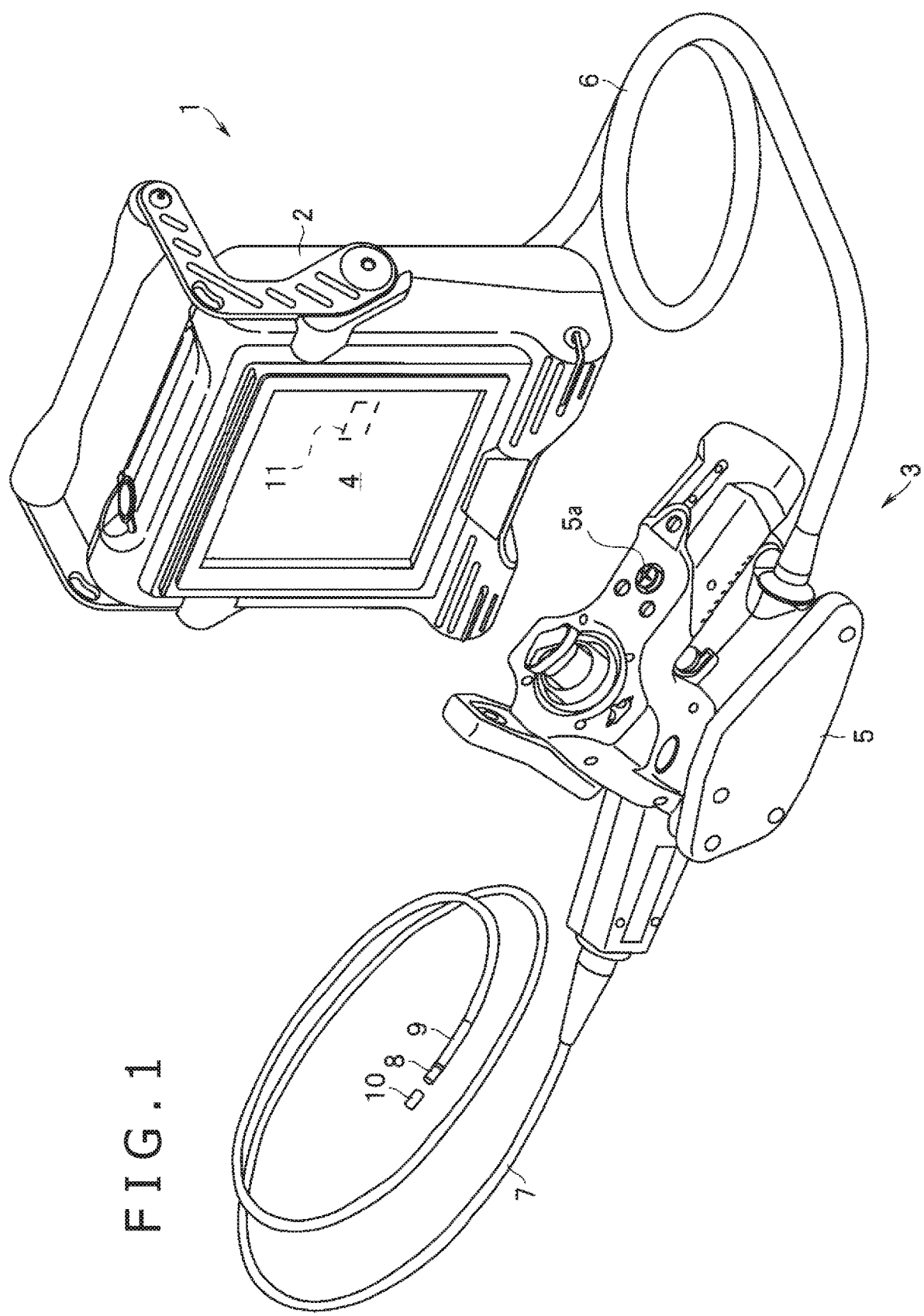
FIG. 1 is a schematic diagram depicting an endoscope device according to a first embodiment of the technology described herein.

FIG. 1 is a schematic diagram depicting an endoscope device according to a first embodiment of the technology described herein. In an endoscopic inspection, this embodiment displays an image (hereafter called "assessment assist image"), which allows to conjure up the criteria for assessment. The assessment is about abnormality such as damage. Such assessment assist images are considered to include past images or reference images, and the like. The past images are endoscopic images acquired in past inspections. The reference images are prepared beforehand as the criteria for assessment. In this embodiment, assessment assist images such as past images are recorded and stored. One of the assessment assist images is retrieved and displayed in view of the kind, rank and the like of damage. Therefore, this embodiment reduces variations in assessments by individual user in inspections and facilitates assessments that conform with the criteria for assessment.

Figure 2:
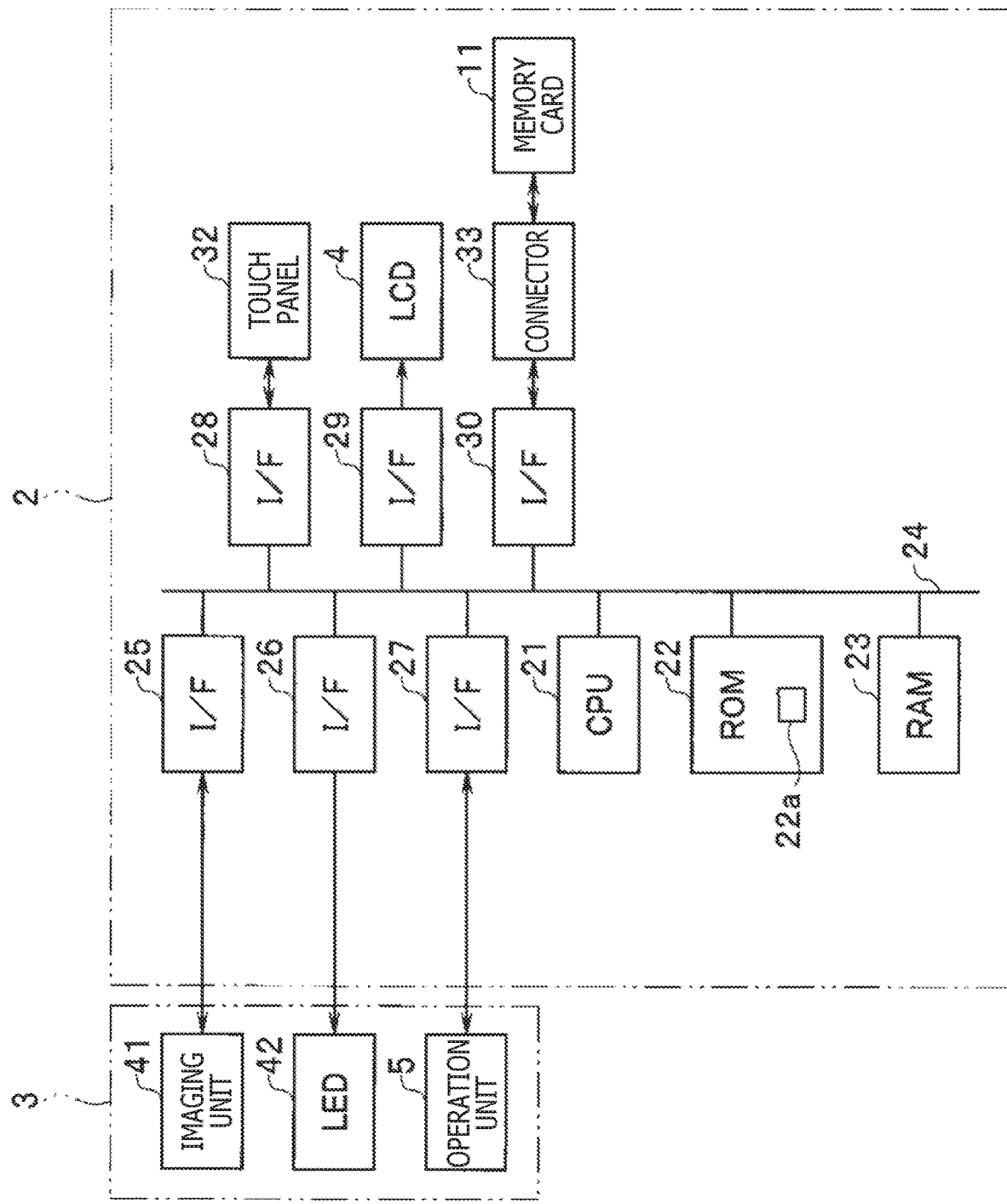
FIG. 2 is a block diagram for illustrating an internal circuit configuration of a device console of the endoscope device depicted in FIG. 1.

In a description hereinafter, past images as endoscopic images are acquired in past inspections and those are recorded and stored. One of the past images is retrieved and displayed in view of the kind, rank and the like of damage. It may, however, be configured to retrieve and display a reference image instead of such a past image. The term "reference image" means a reference image or sketch image that includes the length, width, depth and/or the like of damage written thereon. Based on FIG. 1, a description will first be made about the configuration of an endoscope device 1. As depicted in FIG. 1, the endoscope device 1 is configured including a device console 2 as a main unit and a scope unit 3 that is connected to the device console 2. The device console 2 has a liquid crystal panel 4 (hereinafter abbreviated as "LCD") as a display device. An endoscopic image, an operation menu and the like are displayed on the LCD 4. The LCD 4 is a display unit that displays an endoscopic image thereon. As will be described hereinafter, a touch panel may be arranged on the LCD 4 as best depicted in FIG. 2. However, as one of ordinary skill in the art would appreciate that the touch panel in FIG. 2 is exemplary and other touch panels with various configuration can be used and they are within the scope of the technology disclosed herein. The scope unit 3 has an operation unit 5, and an insert section 7. The insert section 7 is connected to the device console 2 via a universal cable 6 as a connection cable. The insert section 7 is formed of a flexible insert tube. The scope unit 3 is detachably attached to the device console 2 via universal cable 6. An imaging unit is built in a tip portion 8 of the insert section 7. The imaging unit is configured of an imaging device and an imaging optical system. The imaging device is, for example without limiting, a CCD sensor, CMOS sensor or the like. The imaging optical system is, such as lenses without limiting, disposed on the side of an imaging surface of the imaging device. A bendable portion 9 is disposed on the side of a proximal end of the tip portion 8. An optical adapter 10 is detachably attached on the tip portion 8. The operation unit 5 includes various operation buttons such as a freeze button, a record instructions button (hereinafter called "REC button"), an up/down/left/right (U/D/L/R) direction joystick and a bending joystick.

A user is taking an image of an object, recording of a still image, and the like by operating one or more of the various operation buttons on the operation unit 5. If desired to change "the recording destination folder" for an endoscopic image described hereinafter, the user can select a desired recording destination folder by conducting an operation to tilt a joystick 5a in one of upward, downward, leftward and rightward directions. The joystick 5a is attached on the operation unit 5. If the LCD 4 is configured with the touch panel arranged thereon, the user can instruct various operations of the endoscope device 1 by operating the touch panel. Therefore, the touch panel makes up an operation unit that instructs operational details of the endoscope device 1. The image data of an endoscopic image acquired by imaging are inspection data of the inspection object. The image data are stored in a memory card 11 as a recording medium. The memory card 11 is detachably fitted in the device console 2. Moreover, the image data may be configured to store not only endoscopic images but also past images, reference images and the like in the memory card 11 as a data accumulation unit. In this embodiment, the image data are recorded in the memory card 11 that is detachably fitted as the recording medium in the device console 2. The image data may, however, be configured to be recorded in an unillustrated recording medium, such as a flash memory, built in the device console 2. As a further alternative, the recording of the image data may be conducted at an external device of the device console 2 in place of the memory card 11. For example, a file server with a recording medium included as an external device may be adopted. An interface may be included in the device console 2 to perform communications with the file server so that endoscopic images, past images, reference images and the like may be recorded in the file server.

The user can bring the tip portion 8 of the insert section 7 close to an inspection part of an inspection object. The inspection object is, for example, an engine. The inspection part is, for example, a turbine blade. The user can perform imaging of the inspection part to acquire an endoscopic image. The user can display the endoscopic image on the LCD 4. Further, as will be described hereinafter, the user can change the recording destination folder for the endoscopic image while checking folders in the memory card 11 and if necessary, using the joystick 5a of the operation unit 5. The folders are used for recording endoscopic images during inspections. In addition, it is also configured that the user can assess the kind and rank of damage with respect to every endoscopic image and can record the results of the assessment in association with the endoscopic image. Here, this embodiment is configured to display a past image retrieved based on the results of the assessment by the user on a display screen of the LCD 4. Therefore, this embodiment is used in tandem for facilitating an assessment in compliance with the criteria for assessment by reducing a possible variation in the assessment.

Circuit Configuration

FIG. 2 is a block diagram for illustrating an internal circuit configuration of the device console 2 of the endoscope device 1.

The device console 2 includes a central processing unit (hereinafter called "CPU") 21, a ROM 22 and a RAM 23, which are connected to one another via a bus 24. In addition, a plurality of various interfaces (hereinafter called "I/Fs") 25-30 is also connected to the bus 24. The I/F 25 is a driving and receiving circuit. The I/F 25 performs the transmission of a drive signal to an imaging unit 41 in the scope unit 3 and the reception of image signals from the imaging unit 41. The I/F 26 is a drive circuit for transmitting a drive signal to an LED 42 or a lighting device. The I/F 27 is a circuit for receiving various operation signals from the operation unit 5. Such various operation signals from the operation unit 5 include operation signals from the joystick 5a. If the LCD 4 includes the touch panel 32, the I/F 28 is arranged as a circuit for receiving (i) drive signals for the touch panel 32 or the operation unit and (ii) operation signals from the touch panel 32. The I/F 29 is a circuit for supplying image signals to the LCD 4. The CPU 21 or a display control unit controls displays on the LCD 4. The I/F 30 is a circuit for performing writing of image signals to the memory card 11 and reading of image signals from the memory card 11. The I/F 30 is connected to the memory card 11 via a connector 33 disposed in the device console 2. The memory card 11 is detachably fitted in the connector 33. Each I/F is operated under the control of the CPU 21. When the endoscope device 1 is actuated, the CPU 21 outputs various drive signals to the imaging unit 41 via the I/F 25, and the imaging unit 41 outputs image signals to the CPU 21. The CPU 21 outputs drive instruction signal for the LED 42 to the I/F 26. The LED 42 is driven by an output from the I/F 26 to illuminate an object. As a result, a live image is displayed on the LCD 4.

The operation unit 5 is connected to the CPU 21 via the I/F 27. The operation unit 5 receives user's instructions or operation commands to supply various operation signals to the CPU 21 based on the user's instructions. For example, if the user presses such a freeze button as will be described hereinafter, the CPU 21 creates a still image based on image signals from the imaging unit 41. If the user then presses the REC button, the image data of the still image are recorded in the memory card 11. Since the frozen still image is displayed on the LCD 4, the user can check the still image and, if desired to record the still image, presses the REC button.

Folder and File Name

Within the memory card 11, desired folders are created by the CPU 21 or the like based on user's instruction or command. By using an unillustrated personal computer, for example, the user may create a plurality of folders in the memory card 11, which may have a hierarchical structure before an endoscopic inspection. For example, the user can create a plurality of folders having a hierarchical structure under desired folder names under a "root" folder in the memory card 11. As will be described hereinafter, an endoscopic image is acquired as a result of imaging by the imaging unit 41 in the scope unit 3. The user can then record the endoscopic image in desired one of the folders in the memory card 11. The hierarchical structure of folders can be created in the memory card 11. The names of the folders and the names of files of endoscopic images can be stored in the individual folders. The hierarchical structure and the names can be set appropriately according to inspection objects, inspection parts and the like. Based on the appropriate hierarchical structure and the names, it is possible to easily determine, from each file name and folder name, of which inspection object, inspection part and like each endoscopic image is contained there.

FIG. 3 is an illustration examples of folders having such a hierarchical structure. FIG. 3 schematically expresses the respective folders and files contained in the folders to describe the folders having the hierarchical structure. In this respect, FIG. 3 illustrates an example of folders each having two hierarchical layers, that is, two levels. As illustrated in FIG. 3, the "root" folder is created in the memory card 11. Under this "root," there is a folder "DCIM," and under the folder "DCIM," there is a subfolder "IV70001." Further, under the "root" a folder "ENGINE1_SN001" is created. Under the folder "ENGINE1_SN001," three subfolders "HPC_STAGE1_ZONE1_1," "HPC_STAGE1_ZONE1_2" and "HPC_STAGE1_ZONE2_1" are created. Furthermore, under the "root" a folder "ENGINE2_SN002" is also created. Under the folder "ENGINE2_SN002," two subfolders "HPC_STAGE1_ZONE1_1" and "HPC_STAGE1_ZONE1_3" are created. "ENGINE1" and "ENGINE2" in "ENGINE1_SN001" and "ENGINE2_SN002" in the folders are, for example, engine names. "SN001" and "SN002" are serial numbers or the like. "ENGINE1_SN001" and "ENGINE2_SN002" indicate inspection parts, respectively.

Under the "root" in the memory card 11, the user creates folders under desired names beforehand. The user may perform this folder creation work through an external device such as a personal computer or by connecting a hardware keyboard to the endoscope device 1 and operating the hardware keyboard. As a further alternative, the user may perform the creation work of the folders by operating a settings screen displayed on the LCD 4 and a software keyboard configured as a graphical user interface (GUI). As a still further alternative, if the LCD 4 is configured with the touch panel 32 arranged thereon, the user may use a settings screen displayed on the LCD 4 and may perform the creation work of the folders by operating the touch panel 32 or the like. As will be described hereinafter, the user can select, as a recording destination folder for an endoscopic image, desired one of the plural folders created beforehand as described above. In the selected folder, the user can record the endoscopic image after its acquisition. Each folder has two hierarchical layers, but may have three or more hierarchical layers. Further, as indicated by dotted lines in FIG. 3, three or more folders may be contained in the same hierarchical layer. In addition, the folder is not necessarily needed to have two or more hierarchical layers, but may have an architecture having only one hierarchical layer under the "root". In this embodiment, it is configured (i) to acquire an endoscopic image by an endoscopic inspection of each inspection part, (ii) to assess the kind of damage and the degree, in other words, rank of damage in every endoscopic image, and (iii) to add information on the kind and rank of damage as inspected results of the abnormality to the image file of the endoscopic image.

FIG. 3 illustrates the example that the image files of endoscopic images are stored and the images are already assessed and added with inspected results. In the example of FIG. 3, it is illustrated that a plurality of image files of endoscopic images are recorded in the JPEG format in each of three folders "HPC_STAGE1_ZONE1_1," "HPC_STAGE1_ZONE1_2" and "HPC_STAGE1_ZONE2_1." The file names contained in each folder are each composed of the folder names of the upper and lower hierarchical layers, and a file mark and a serial number added thereto. A file mark is a predetermined mark that is added to a file name to be recorded. The file mark functions as an identification mark, and indicates, for example, the rank of damage. Therefore, the file name is set as "top-layer folder name_subfolder name_file mark_serial number.jpg." For example, by connecting the folder name of the top-level folder "ENGINE1_SN001" and the folder name of the subfolder "HPC_STAGE1_ZONE1" via a symbol "_" (under bar) and by adding the file mark "A" and the serial number "001" further, the file name "ENGINE1_SN001_HPC_STAGE1_ZONE1_1_A_001.jpg" is created. The example of FIG. 3 indicates the addition of four kinds of file marks, "A," "B," "C" and "D." "A" represents a rank "acceptable (Accept)," "B" represents a rank "replacement needed (Reject)," "C" represents a rank "repair needed (Repair)," and "D" represents a rank "re-inspection needed (Re-Inspect)." As a file mark, "X" (No Mark) may also be set. In the example of FIG. 3, each file mark is a single character, but may be plural characters or a string of characters such as "ACCEPT" or "REPAIR."

As examples of damage to be assessed upon inspection, there are kinds such as surface defects, e.g., chips, dents and peeling, cracks, and corrosion. In this embodiment, information on the kind of damage is also added to the image file of each endoscopic image. The information on the kind of damage may be stored, for example, in an EXIF field of the image file.

The CPU 21 performs processing for (i) driving the imaging unit 41, (ii) displaying an image, which is captured by the imaging unit 41, on the display screen of the LCD 4, (iii) specifying an inspection folder in which an endoscopic image, or endoscopic image, is to be recorded, and (iv) specifying the kind and rank of damage. In addition, the CPU 21 is also configured such that, if the kind and rank of damage is specified, a retrieval program is executed to perform "assessment assist image display processing." The retrieval program is recorded at a retrieval program area 22a of the ROM 22. In the "assessment assist image display processing", a past image is retrieved and displayed as an "assessment assist image" if the information added with the past image matches the kind and rank of damage specified by the user. With reference to the assessment assist image displayed by this "assessment assist image display processing", each user can easily determine whether an assessment is conducted in compliance with the criteria for assessment.

With a view to facilitating of specifying the position of damage upon assessment, a mark such as a (i) circle surrounding the position of the damage or an arrow indicating the position of the damage, (ii) text comments on the damage, (iii) a hand-written sign specifying the damage, or the like can be added to each assessment assist image. Such information may be recorded, for example, at an EXIF area rather than in the image file of the assessment assist image. In this case, such information can be displayed in superimposition upon displaying the assessment assist image, or can be set invisible. The CPU 21 can also appropriately set a display method for the assessment assist image.

Figure 4:
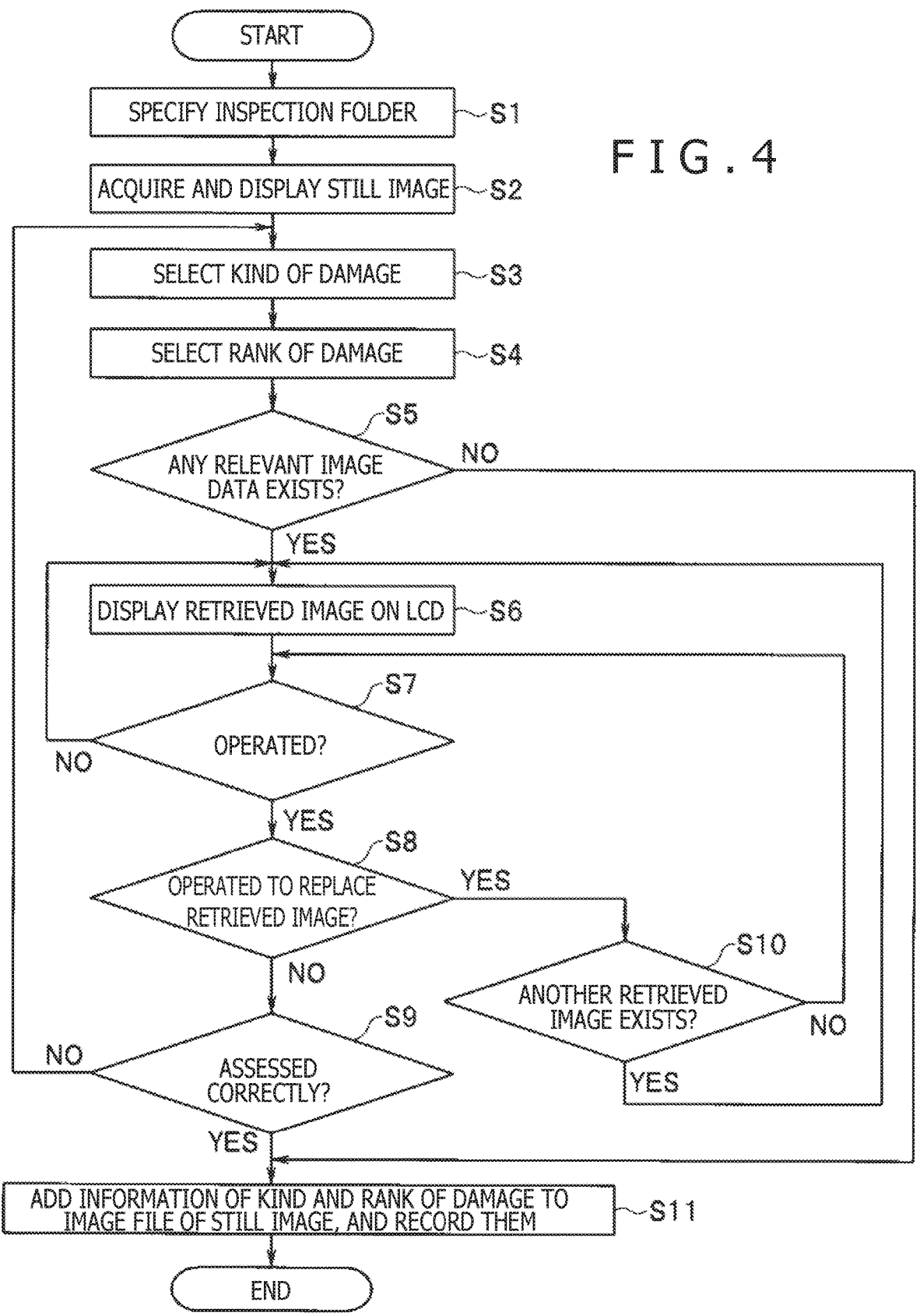
FIG. 4 is a flowchart for describing operation of the endoscope device of FIG. 1.
Figure 5:
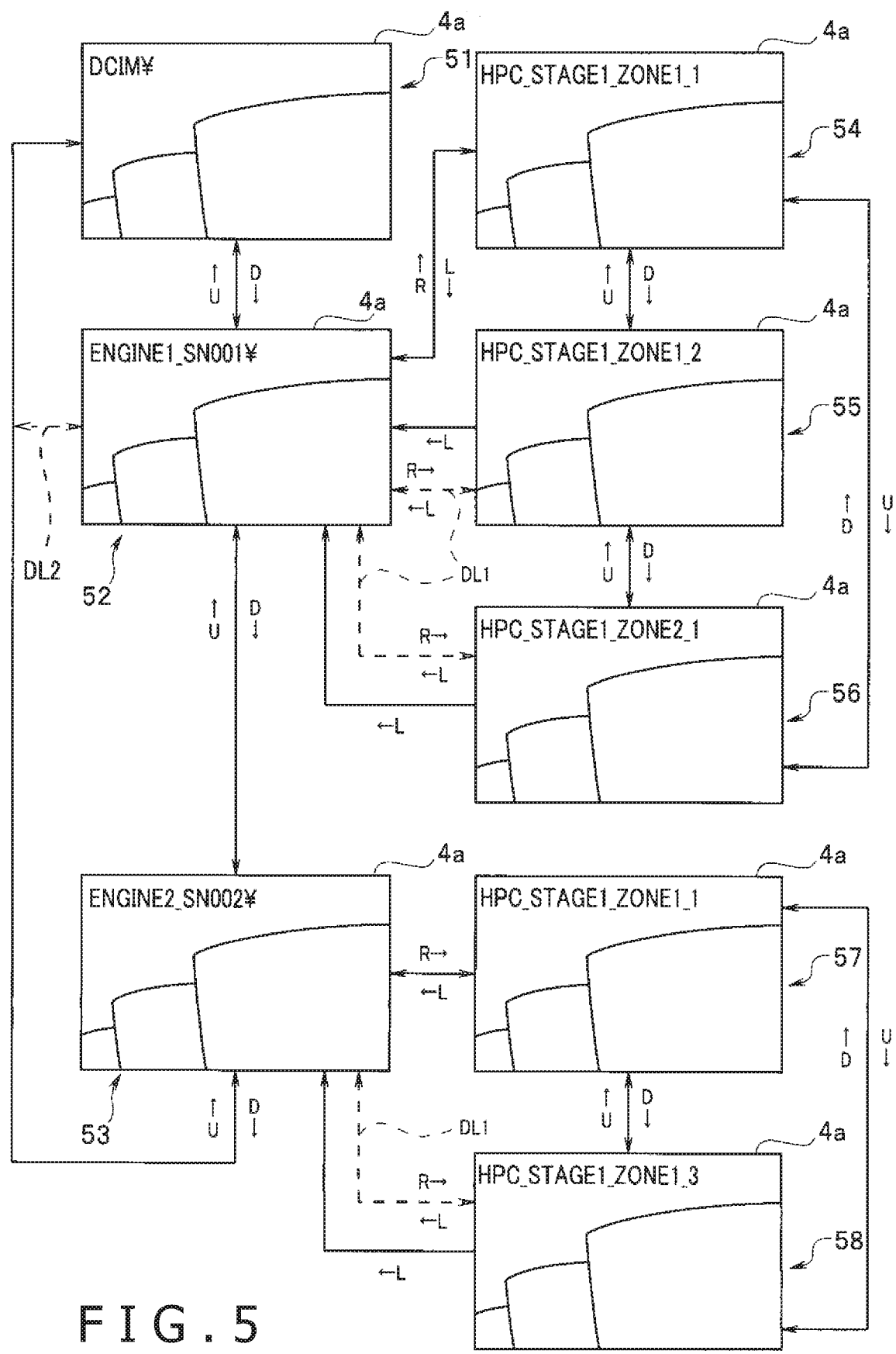
FIG. 5 is an illustration of examples of screen displays upon conducting an operation to specify an inspection folder in the operation of the endoscope device of FIG. 1.
Figure 6:
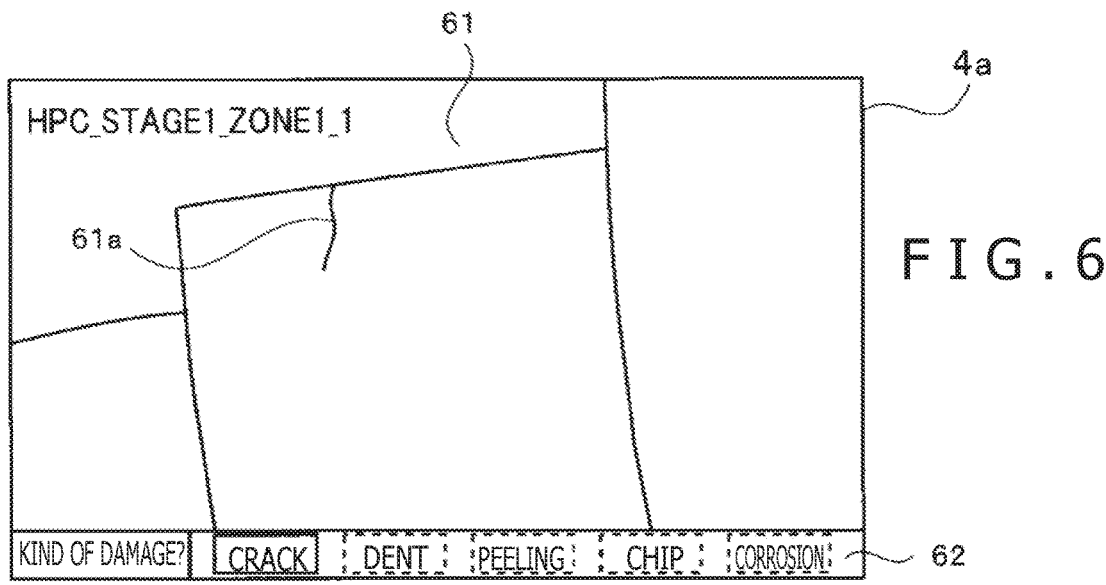
FIG. 6 is an illustration of an example of a screen display upon selection of a kind of damage in the operation of the endoscope device of FIG. 1.
Figure 7:
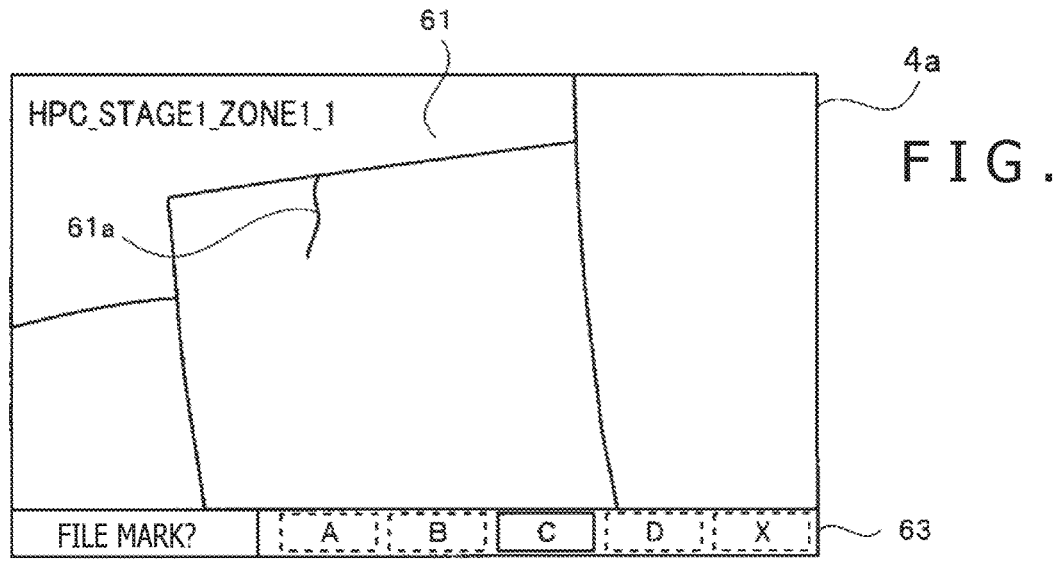
FIG. 7 is an illustration of an example of a screen display upon selection of a rank of damage in the operation of the endoscope device of FIG. 1.
Figure 8:
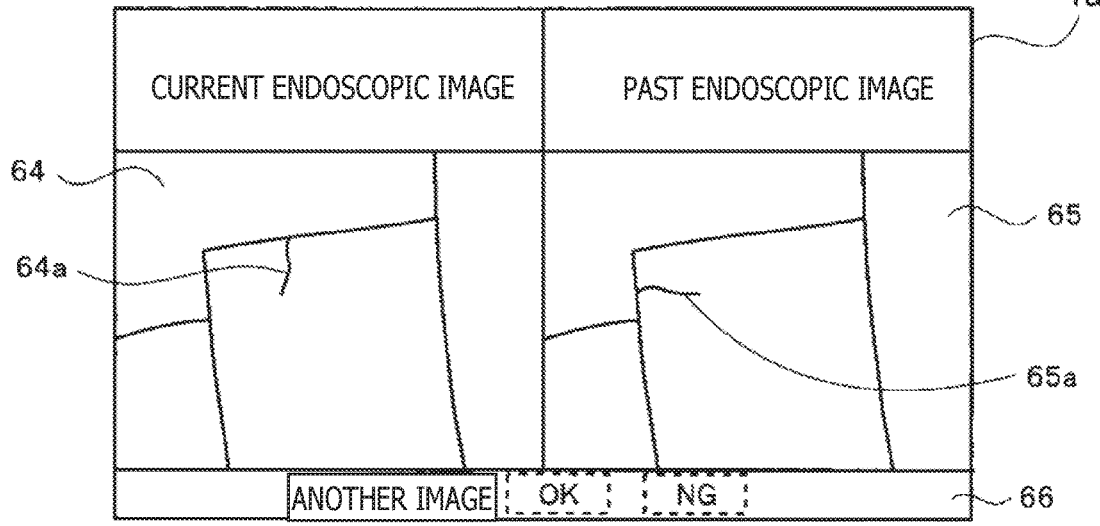
FIG. 8 is an illustration of an example of a screen display of a still image and an assessment assist image in the operation of the endoscope device of FIG. 1.

With reference to FIGS. 4 through 8, a description will next be made about the operation of this embodiment configured as described hereinbefore. FIG. 4 is a flowchart for describing the operation of the first embodiment. FIG. 5 is an illustration of examples of screen displays upon conducting an operation to specify an inspection folder. FIG. 6 is an illustration of an example of a screen display upon selection of a kind of damage. FIG. 7 is an illustration of an example of a screen display upon selection of a rank of damage. FIG. 8 is an illustration of an example of a screen display of a still image and an assessment assist image. If power is applied to the device console 2 to enable imaging by the imaging unit 41, an endoscopic image is captured by the imaging unit 41 and the CPU 21 controls the display unit 4 so as to display the endoscopic image as a live image on the display screen of the LCD 4. The CPU 21 then receives an operation from the operation unit 5. The operation specifies an inspection folder, in which the endoscopic image, or endoscopic image, is to be recorded. The CPU 21 specifies the inspection folder based on the user's operation in step 1.

FIG. 5 illustrates examples of screen displays and screen transitions when an inspection folder is specified. The user performs an inspection while watching a live image of an inspection object as an illustrative example, but not limiting, a turbine blade in FIG. 5 displayed on the screen. On the display screen 4a of the LCD 4, the live image and the name of its recording destination folder (inspection folder) are displayed. After the power supply is turned on, the "DCIM" folder under the "root" is set beforehand as the recording destination folder. Therefore, as illustrated on a screen 51, "DCIM\" is displayed as a recording destination folder on the display screen 4a shortly after the power supply is turned on. On the screen 51 of FIG. 5, information "DCIM\" is displayed in the upper left of the display screen 4a. The information indicates a folder of "DCIM" as the recording destination folder. On another screen 52 and the like, information with the name of a recording destination folder is also displayed in the upper left of the display screen 4a. However, the position of such information is not required to be the upper left of a screen, but may be, for example, in the upper right of the screen. In the case of FIG. 5, the mark "¥" is added, as information that indicates the recording destination folders, to the folder names of the recording destination folders on the screens 51 and 52 and a screen 53. However, a mark other than the mark "¥" may be used or the mark "¥" may be omitted. Also in the case of FIG. 5, the information that indicates the recording destination folders include the folder names of the recording destination folders, but may exclude the folder names of the recording destination folders insofar as the user can recognize and discriminate the recording destination folders.

If desired to record a still image in a desired folder which is created beforehand, the user can select the folder by operating the joystick 5a. If the joystick 5a is tilted in one of the directions including the upward (U), downward (D), leftward (L) and rightward (R), the desired folder is selected from the plural folders having a hierarchical structure according to the tilted direction, and is set at the recording destination folder.

Additionally, FIG. 5 represents screen transitions upon selection of a recording destination file from a group of folders illustrated in FIG. 3 and having the two hierarchical layers each including two folders created under the hierarchical layer. The order of displaying the recording destination folders in the respective hierarchical layers is set beforehand so that they are displayed in a predetermined order such as the creation dates and times of the folders or the alphabetical order of the folder names. The folder "ENGINE1_SN001" is the next folder of "DCIM" in the same hierarchical layer and the folder "ENGINE1_SN001" is described under the folder "DCIM" in FIG. 3. Therefore, if the joystick 5a is tilted downward, specifically tilted in the direction "D" as illustrated in FIG. 5 by arrow, in the state of the screen 51, the folder "ENGINE1_SN001" is selected as a recording destination folder. The screen transitions from the screen 51 to the screen 52. The folder "DCIM" is the preceding folder of "ENGINE1_SN001" in the same hierarchical layer and the folder "DCIM" is described above the folder "ENGINE1_SN001" in FIG. 3. Therefore, if the joystick 5a is tilted upward, specifically tilted in the direction "U" as illustrated in FIG. 5 by arrow, in the state of the screen 52, the folder "DCIM" is selected as a recording destination folder. Therefore, the screen would transition from the screen 52 to the screen 51, accordingly.

The folder "ENGINE2_SN002" is the next folder of the folder "ENGINE1_SN001" in the same hierarchical layer. Therefore, if the joystick 5a is tilted downward, specifically tilted in the direction "D" as illustrated in FIG. 5 by arrow, in the state of the screen 52, the folder "ENGINE2_SN002" is selected as a recording destination folder. Thus, the screen would transition from the screen 52 to the screen 53, accordingly. The folder "DCIM" is the first folder in the same hierarchical layer. If the joystick 5a is tilted downward, specifically tilted in the direction "D" as illustrated in FIG. 5 by arrow, in the state of the screen 53, the folder "DCIM" is selected as a recording destination folder. Therefore, the screen would transition from the screen 53 to the screen 51, accordingly. Further, the folder "HPC_STAGE1_ZONE1_1" is the first folder in the lower hierarchical layer and the folder is described as the uppermost folder in FIG. 3. Therefore, if the joystick 5a is tilted rightward, specifically tilted in the direction "R" as illustrated in FIG. 5 by arrow, in the state of the screen 52, the folder "HPC_STAGE1_ZONE1_1" is selected as a recording destination folder. Thus, the screen would transition from the screen 52 to a screen 54, accordingly. Furthermore, the folder "ENGINE1_SN001" is a folder in the upper hierarchical layer of the folder "HPC_STAGE1_ZONE1_1". Therefore, if the joystick 5a is tilted leftward, specifically tilted in the direction "L" as illustrated in FIG. 5 by arrow, in the state of the screen 54, the folder "ENGINE1_SN001" is selected as a recording destination folder. Therefore, the screen would transition from the screen 54 to the screen 52.

The folder "HPC_STAGE1_ZONE1_2" is the next folder of the folder "HPC_STAGE1_ZONE1_1" in the same hierarchical layer. Therefore, if the joystick 5a is tilted downward, specifically tilted in the direction "D" as illustrated in FIG. 5 by arrow, in the state of the screen 54, the folder "HPC_STAGE1_ZONE1_2" is selected as a recording destination folder. Therefore, the screen would transition from the screen 54 to a screen 55. The folder "HPC_STAGE1_ZONE1_1" is the preceding folder of the folder "HPC_STAGE1_ZONE1_2" in the same hierarchical layer. Therefore, if the joystick 5a is tilted upward, specifically tilted in the direction "U" as illustrated in FIG. 5 by arrow, in the state of the screen 55, the folder "HPC_STAGE1_ZONE1_1" is selected as a recording destination folder. Thus, the screen would transition from the screen 55 to the screen 54, accordingly. The folder "HPC_STAGE1_ZONE2_1" is the next folder of "HPC_STAGE1_ZONE1_2" in the same hierarchical layer. Therefore, if the joystick 5a is tilted downward, specifically tilted in the direction "D" as illustrated in FIG. 5 by arrow, in the state of the screen 55, the folder "HPC_STAGE1_ZONE2_1" is selected as a recording destination folder. Therefore, the screen would transition from the screen 55 to a screen 56. The folder "HPC_STAGE1_ZONE1_2" is the preceding folder of the folder "HPC_STAGE1_ZONE2_1" in the same hierarchical layer. Therefore, if the joystick 5a is tilted upward specifically tilted in the direction "U" as illustrated in FIG. 5 by arrow, in the state of the screen 56, the folder "HPC_STAGE1_ZONE1_2" is selected as a recording destination folder. Thus, the screen would transition from the screen 56 to the screen 55.

The folder "HPC_STAGE1_ZONE2_1" is the last folder in the same hierarchical layer. Therefore, if the joystick 5a is tilted upward, specifically tilted in the direction "U" as illustrated in FIG. 5 by arrow, in the state of the screen 54, the folder "HPC_STAGE1_ZONE2_1" is selected as a recording destination folder. Therefore, the screen would transition from the screen 54 to the screen 56, accordingly. The folder "HPC_STAGE1_ZONE1_1" is the first folder in the same hierarchical layer. Therefore, if the joystick 5a is tilted downward specifically tilted in the direction "D" as illustrated in FIG. 5 by arrow, in the state of the screen 56, the folder "HPC_STAGE1_ZONE1_1" is selected as a recording destination folder. Therefore, the screen transitions from the screen 56 to the screen 54, accordingly.

Still furthermore, the folder "ENGINE1_SN001" is a folder in the upper hierarchical layer of the folder "HPC_STAGE1_ZONE1_2" and the folder "HPC_STAGE1_ZONE2_1". Therefore, if the joystick 5a is tilted leftward, specifically tilted in the direction "L" as illustrated in FIG. 5 by arrow, in the state of the screen 55 or screen 56, the folder "ENGINE1_SN001" is selected as a recording destination folder. Thus, the screen would transition from the screen 55 or screen 56 to the screen 52. Screen transitions among the folder "ENGINE2_SN002" and the two subfolders "HPC_STAGE1_ZONE1_1" and "HPC_STAGE1_ZONE1_3" also take place, as illustrated in FIG. 5, among the screen 53 and screens 57 and 58. That is the same manner as in the screen transitions among the screens 52 and 54 to 56. Therefore, the user can check the recording destination files and can easily change them while watching the live images. The joystick 5a is a joystick for changing or selecting the recording destination folder, but in a switched mode, a joystick for use in bending operations may be used as an operation device for the selection of recording destination folders. In the case of FIG. 5, if the joystick 5a is tilted rightward, specifically tilted in the direction "R" as illustrated in FIG. 5 by arrow, in the state of the screen 52 or 53 after the screen has transitioned from the screen 55 or 56 to the screen 52 or from the screen 58 to the screen 53, the screen transitions from the screen 52 to the screen 54 or from the screen 53 to the screen 57 so that the folder "HPC_STAGE1_ZONE1_1" which is the first folder in the lower hierarchical layer is selected as a recording destination folder. It may, however, be configured such that, if the joystick 5a is tilted rightward, specifically tilted in the direction "R" as illustrated in FIG. 5 by arrow, in the state of the screen 52 or 53 after the screen has transitioned from the screen 55 or 56 to the screen 52 or from the screen 58 to the screen 53, the screen 55 or 56 or the screen 58 may be displayed as indicated by a dashed line DL1 in FIG. 5. For this configuration, the folder data of the transitioned screens are stored beforehand in the RAM 23, and the CPU 21 controls the screen display to display the folder before the transition. In the case of FIG. 5, the folder "DCIM" is selected or set as a recording destination folder by default. However, desired one of the folders in the uppermost layer other than the folder "DCIM," for example, the folder "ENGINE1_SN001" as the first folder may be selected by default.

To move to a folder in the same hierarchical layer, it may be configured to make a selection between the folders other than "DCIM" in the uppermost layer. Specifically, it may be configured (i) that, if the joystick 5a is tilted downward, specifically tilted in the direction "D" as illustrated in FIG. 5 by arrow, in the state of the screen 53 as indicated by a dashed line DL2 in FIG. 5, the screen transitions to the screen 52 and (ii) that, if the joystick 5a is tilted upwards specifically tilted in the direction "U" as illustrated in FIG. 5 by arrow, in the state of the screen 52, the screen would transition to the screen 53. In this embodiment, only the folder name in the hierarchical layer which is currently under selection is displayed on the screen. It may, however, be configured such that, when desired to display, for example, a folder name in a lower hierarchical layer, a folder name in its upper hierarchical layer is also displayed in combination. In this case, the folder name, for example, on the screen 54 is "ENGINE1_SN001\HPC_STAGE1_ZONE1_1." After specifying a desired inspection folder, the user brings the tip portion 8 of the insert section 7 close to an inspection part, and depresses the freeze button. As a consequence, the imaging unit 41 acquires a still image of the inspection part, and supplies it to the CPU 21 via the I/F 25. The CPU 21 controls the RAM 23 so as to store the acquired still image in the RAM 23, and at the same time, delivers it to the LCD 4 via the I/F 29 to display the still image (endoscopic image) in step S2. In this embodiment, in step 3, the CPU 21 controls the LCD 4 so as to display a menu for the selection of a kind of damage on the display screen 4a of the LCD 4, on which the endoscopic image is displayed.

FIG. 6 illustrates an example of a display in this case. On the display screen 4a, an endoscopic image 61 is displayed, and a menu 62 for the selection of a kind of damage is also displayed. FIG. 6 indicates that a crack 61a occurred in a turbine blade in the endoscopic image 61. Further, FIG. 6 illustrates five kinds of damage, which are a crack, a dent, peeling, a chip and corrosion, as examples that can be specified as kinds of damage, although the kinds of damage shall not be limited to them. The user assesses the kind of damage with respect to the crack 61a in the endoscopic image 61, and specifies results of the assessment. For example, the user may select which one of the following kinds of damage: a crack, a dent, peeling and corrosion the damage is by tilting the joystick 5a of the operation unit 5 in the direction L or R, and may then operate an unillustrated select button to specify the kind of damage. In FIG. 6, the solid line indicates a selected kind, while the broken lines indicate unselected kinds. Upon completion of the operation to specify the kind of damage by the user, the CPU 21 controls the RAM 23 so as to store information on the specified kind of damage in the RAM 23, and in the next step S4, displays a menu for the selection of a rank of damage on the display screen 4a of the LCD 4, on which the endoscopic image is displayed.

FIG. 7 illustrates an example of a display in this case. On the display screen 4a, the endoscopic image 61 is displayed. A menu 63 for the selection of a damage rank to be specified as a file mark is also displayed. FIG. 7 illustrates the above-described five ranks of damage, which are A, B, C, D and X, as examples that can be specified as ranks of damage, although the ranks of damage shall not be limited to them. With respect to the crack 61a in the endoscopic image 61, the user assesses the rank of damage, and specifies the assessment results. For example, the user may select one of the damage ranks A, B, C, D and X by tilting the joystick 5a on the operation unit 5 in the direction L or the direction R. The user may then operate the unillustrated select button to specify the rank of damage. In FIG. 7, the solid line indicates a selected rank, while the broken lines indicate unselected ranks. Upon completion of an operation to specify the rank of damage identified by the user, the CPU 21 controls the RAM 23 so as to store information on the specified rank (file mark) of damage in the RAM 23. The CPU 21 allows the processing to proceed to the next step S5. The results of the user's assessment on the abnormality such as damage of the inspection object are not confirmed yet at this stage. In this embodiment, to reduce variations in assessment among individual users, an "assessment assist image" is displayed based on the results of the user's assessment so as to allow the user to relatively easily determine whether the results of his or her own assessment are correct. By visually comparing the endoscopic image and the "assessment assist image" with each other, the user can easily determine whether the assessment is correct or incorrect.

Described specifically, the CPU 21 performs retrieval over the past images by using, as retrieval keys, the kind and rank of damage specified by the user. For example, the kind and rank of damage is specified by the user and the information on the kind and rank is added to the image files. The CPU 21 retrieves over the image files in a currently-specified inspection folder, and obtains an image, or assessment assist image, as the results of the retrieval. As described hereinbefore, the rank of damage can be easily retrieved according to the file name. On the other hand, the kind of damage is recorded at an EXIF field in each image file, and therefore, can be retrieved by examining the image file. Since extended time is needed for the examination of each EXIF field, an index file may be prepared and stored beforehand at a predetermined area in the memory card 11. The index file indicates correspondence relationships between individual image files and the kinds of the corresponding damage. By retrieval processing of the index file, an image file is retrieved if the specified kind of damage is same as information on the kind of damage added to the image file. Although the information on the kind of damage is described to be recorded at the EXIF field, the information on the kind of damage may be included in the file name. In this case, an "assessment assist image" can be easily obtained by performing retrieval over file names while using the kind and rank of damage as retrieval keys. Although the CPU 21 is described to retrieve the "assessment assist image" from the currently-specified inspection folder, the CPU 21 may retrieve an "assessment assist image" from another inspection folder in the same hierarchical layer or may retrieve an "assessment assist image" from another folder in an upper hierarchical layer.

If no assessment assist image can be retrieved in the retrieval that used, as retrieval keys, the kind and rank of damage specified by the user, the CPU 21 (i) allows the processing to proceed from step S5 to step S11, (ii) confirms the kind and rank of damage specified by the user, (iii) adds this information to the image file of the still image, and then (iv) controls the memory card 11 so as to store the image file along with the information in the memory card 11. If a relevant image file is found to exist as a result of the retrieval, the CPU 21 controls the LCD 4 so as to display the "assessment assist image" on the display screen 4a of the LCD 4 in step S6.

FIG. 8 illustrates an example of a display in the aforementioned case. A current endoscopic image 64 and an assessment assist image 65 retrieved from past images are displayed on the display screen 4*a*. The current endoscopic image 64 corresponds to the endoscopic image 61 in FIGS. 6 and 7, and a crack 64*a* corresponds to the crack 61*a*. In the assessment assist image 65, an image portion of a crack 65*a* occurred in a turbine blade is also contained. Although, in the one embodiment of the technology disclosed herein, a turbine blade is used to illustrate one of the advantages utility of the endoscope device 1, but one of ordinary skill in the art would appreciate that the endoscope device 1 can be used for variety of other diagnostics endeavor. In addition, the CPU 21 also controls the LCD 4 so as to display, at a lower end of the display screen 4*a*, an "assessment specifying menu" 66 for specifying whether the assessment by the user is correct or incorrect. In the example of FIG. 8, as the assessment specifying menu 66, a menu of three choices is displayed including "ANOTHER IMAGE" for displaying another assessment assist image, "OK" indicating that the assessment by the user is correct, and "NG" indicating that an assessment is to be conducted again without adopting the current assessment by the user. In FIG. 8, the solid line indicates a selected choice, while the broken lines indicate unselected choices. By comparing the conditions of the crack 64*a* in the current endoscopic image 64 with the conditions of the crack 65*a* of the retrieved assessment assist image 65, the user determines whether his or her own assessment about the kind and rank of damage is correct or incorrect. If desired to test another assessment assist image, the user selects "ANOTHER" as a command in the "assessment correctness/incorrectness specifying menu" 66 to make the CPU 21 control the LCD 4 so as to perform displaying the another assessment assist image.

The CPU 21 determines in step S7 whether there has been any operation by the user. If there is user's operation, the CPU 21 determines in step S8 whether the user's operation is an operation to replace the assessment assist image, and determines in step S9 whether the user's operation is an operation to specify the correctness or incorrectness of his or her own assessment. If the user conducts an operation to specify "ANOTHER", the CPU 21 allows the processing to proceed from step S8 to step S10, where a determination is made as to whether there is another assessment assist image. If another assessment assist image exists, the CPU 21 returns the processing to step S6, and displays the another assessment assist image. If another assessment assist image does not exist, the CPU 21 returns the processing to step S7, and remains in a standby state for an operation by the user. If the user conducts an operation to specify "NO" in FIG. 8, the CPU 21 returns the processing from step S9 to step S3. Stated specifically, the CPU 21 allows the user to select the kind and rank of damage again in steps S3 and S4. The CPU 21 again retrieves and displays a past image corresponding to the kind and rank of damage specified by the user, and assists the user in determining whether the assessment is correct or not. If the user conducts an operation to specify "OK" in FIG. 8 or an operation to depress the REC button, the CPU 21 allows the processing to proceed from step S9 to step S11, and confirms the kind and rank of damage, or the assessment results, specified by the user to obtain inspection results. The CPU 21 adds information on the confirmed kind and rank of damage to the image file of the endoscopic image (still image) from the imaging unit 41. The CPU 21 controls the memory card 11 so as to record them in the memory card 11. By comparing the currently-acquired endoscopic image with the past image having the same kind and rank of damage, the user can relatively easily perform the inspection in compliance with the criteria for assessment.

In FIGS. 6 to 8, illustrated are the examples that the "button menus" for user's "selection operations" and the like are displayed at the lower end of the display screen 4*a*. However, these button menus may also be displayed by various display methods such as pop-up window and pull-down menu. The selection and instruction operations in FIGS. 6 to 8 can also be conducted using the touch panel 32 instead of relying upon the operation unit 5 alone. For example, a so-called cross key, up/down/left/right key or the like may be used in place of the joystick 5*a*. As a still further alternative, the selection and instruction operations may be conducted by displaying a cross key, up/down/left/right key or the like, which has been created by software, on the display screen 4*a* of the LCD 4 and operating the selection and instruction operations via the touch panel 32. In the description hereinbefore, as the display method of the assessment assist image, the description was made about the example in which (i) the endoscopic image is displayed on the left side and (ii) the assessment assist image is displayed on the right side. However, the individual displays described hereinafter and displays by combinations thereof may also be adopted. Either an endoscopic image or an assessment assist image is magnified (zoomed in), or its position on the display screen 4*a* of the LCD 4 is moved by scrolling display.

One of an endoscopic image and an assessment assist image is displayed in a full-screen mode, and the other image is displayed as a slave screen without transparency over the one image. The image display area for one of an endoscopic image and an assessment assist image is magnified, and the other image is displayed with reduction. An endoscopic image and an assessment assist image are displayed with their screen display positions switched left and right or up and down. An endoscopic image and an assessment assist image are rotated and displayed. On one of an endoscopic image and an assessment assist image, the other image is displayed transparently in superimposition. In this embodiment, a past image corresponding to the kind and rank of damage specified by the user is displayed for a captured and acquired endoscopic image as described hereinbefore. It is, therefore, possible to assist the user in performing an assessment in compliance with the criteria for assessment.

Figure 9:
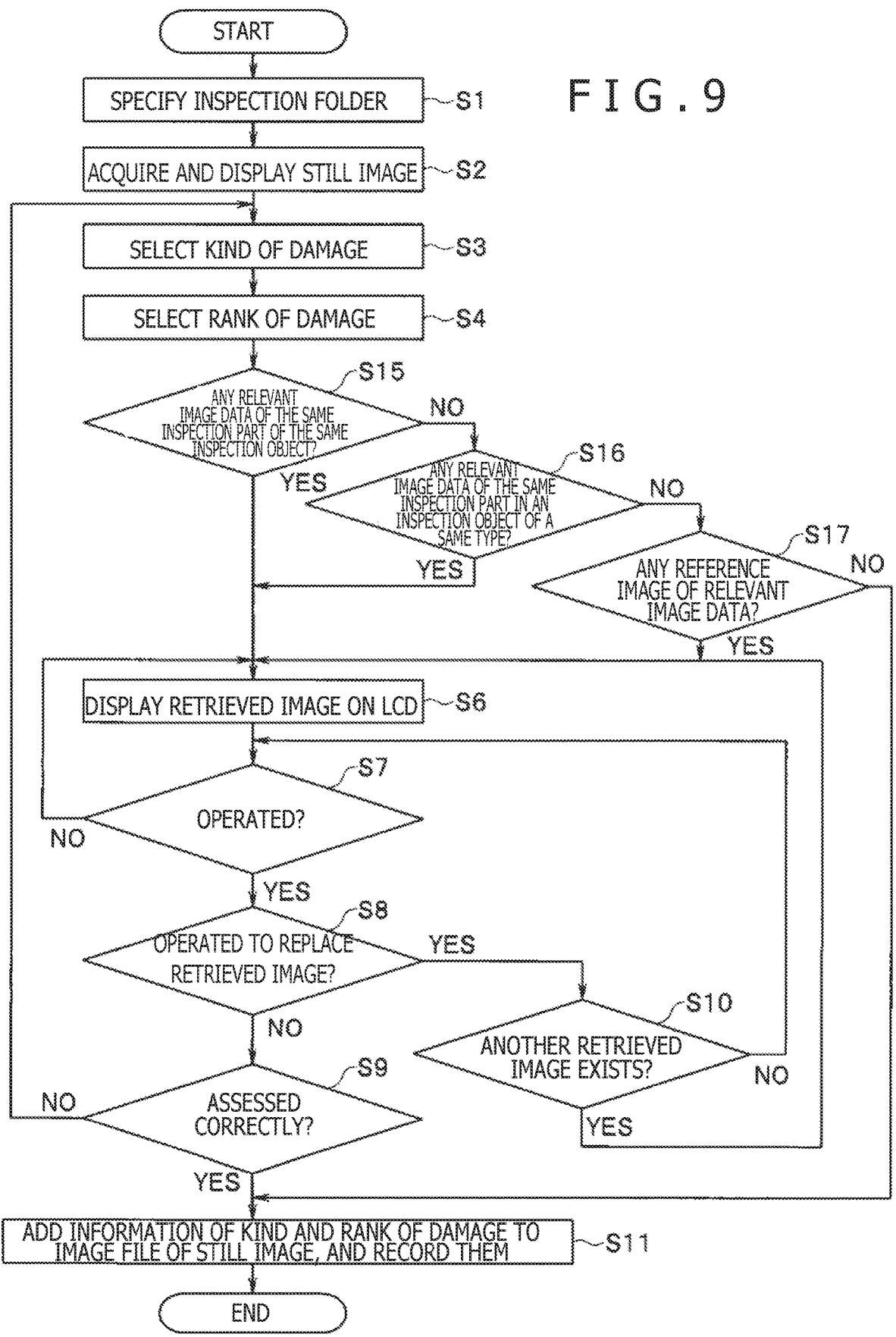
FIG. 9 is a flowchart illustrating operation of an endoscope device according to a first modification of the first embodiment.

FIG. 9 is a flowchart illustrating a first modification of the first embodiment. In FIG. 9, the same procedures as the corresponding ones in FIG. 4 are identified by the same reference symbols and their description is not repeated herein again to avoid redundancy. In the first embodiment described hereinbefore, the description was made about the example that as an assessment assist image, a past image is retrieved and displayed. This first modification illustrates an example that not only a past image but also a reference image is both displayed as assessment assist images. These past image and reference image are displayed according to the predetermined order of priority.

In FIG. 4, it is determined in step S5 whether there is any "assessment assist image" that matches the kind and rank of damage. In FIG. 9 of this first modification, on the other hand, this determination is performed in steps S15 to S17. In step S15, the CPU 21 determines whether there is any "past endoscopic image" that relates to a same inspection part of a same inspection object and matches the kind and rank of damage. If an assessment assist image that relates to a same inspection part of a same inspection object and matches the kind and rank of damage is determined to exist in step S15, the CPU 21 controls LCD 4 so as to display the assessment assist image on the display screen 4*a* of the LCD 4 in step S16.

If there is no assessment assist image of the same inspection part of the same inspection object, the CPU 21 determines in the next step S16 whether there is any past endoscopic image that relates to a same inspection part in an inspection object of a same type and matches the kind and rank of damage. More specifically, the meaning of the inspection object of the same type is, for example, a similar inspection object with different serial number. If exists, the CPU 21 controls the display unit 4 so as to display the past endoscopic image as an assessment assist image on the display screen 4*a*.

If there is not any assessment assist image that relates to a same inspection part in an inspection object of a same type and matches the kind and rank of damage, the CPU 21 determines in the next step S17 whether there is any reference image of the same inspection part, the reference image matching the kind and rank of damage. If exists, the CPU 21 controls to display the reference image as an assessment assist image on the display screen 4*a*. If it is determined in step S17 that there is not any reference image that relates to the same inspection part and matches the kind and rank of damage, the CPU 21 allows the processing to proceed to step S11.

In the first modification of FIG. 9, the description has been made of the example that, only if there is (i) a past image that relates to the same inspection part and matches the kind and rank of damage or (ii) a reference image that relates to the same inspection part and matches the kind and rank of damage, the past image or reference image is displayed as an assessment assist image. However, a past image or reference image that relates to a different inspection part but matches the kind and rank of damage may also be displayed as an assessment assist image if there is such a past image or reference image.

Other operations, functions and effects are similar to those in FIG. 4.

In order to clarify which kind of image is displayed as an assessment assist image, a character display such as "Same Inspection Object," "Inspection Object of Same Type" or "Reference" may be displayed on the assessment assist image. Such an additional display can prevent the user from falsely recognizing the kind of an image displayed as an assessment assist image.

In the first modification, an assessment assist image of a same inspection object, an assessment assist image of an inspection object of a same type, and a reference image are selected and displayed in this order as assessment assist image as described hereinbefore. A past image of the same part of a same inspection object is considered to extremely facilitate an assessment when visually compared with an endoscopic image at the time of an inspection, and therefore is extremely effective as an image to be used as criteria for assessment. On the other hand, a past image of the same part of a same inspection object does not necessary exist, so that the adoption of a past image of an inspection object of a same type rather than a same inspection object as an assessment assist image and the additional use of a reference image can prevent the criteria for assessment from becoming unclear even if there is not any image that can be used as a criterion for assessment in an inspection.

Figure 10:
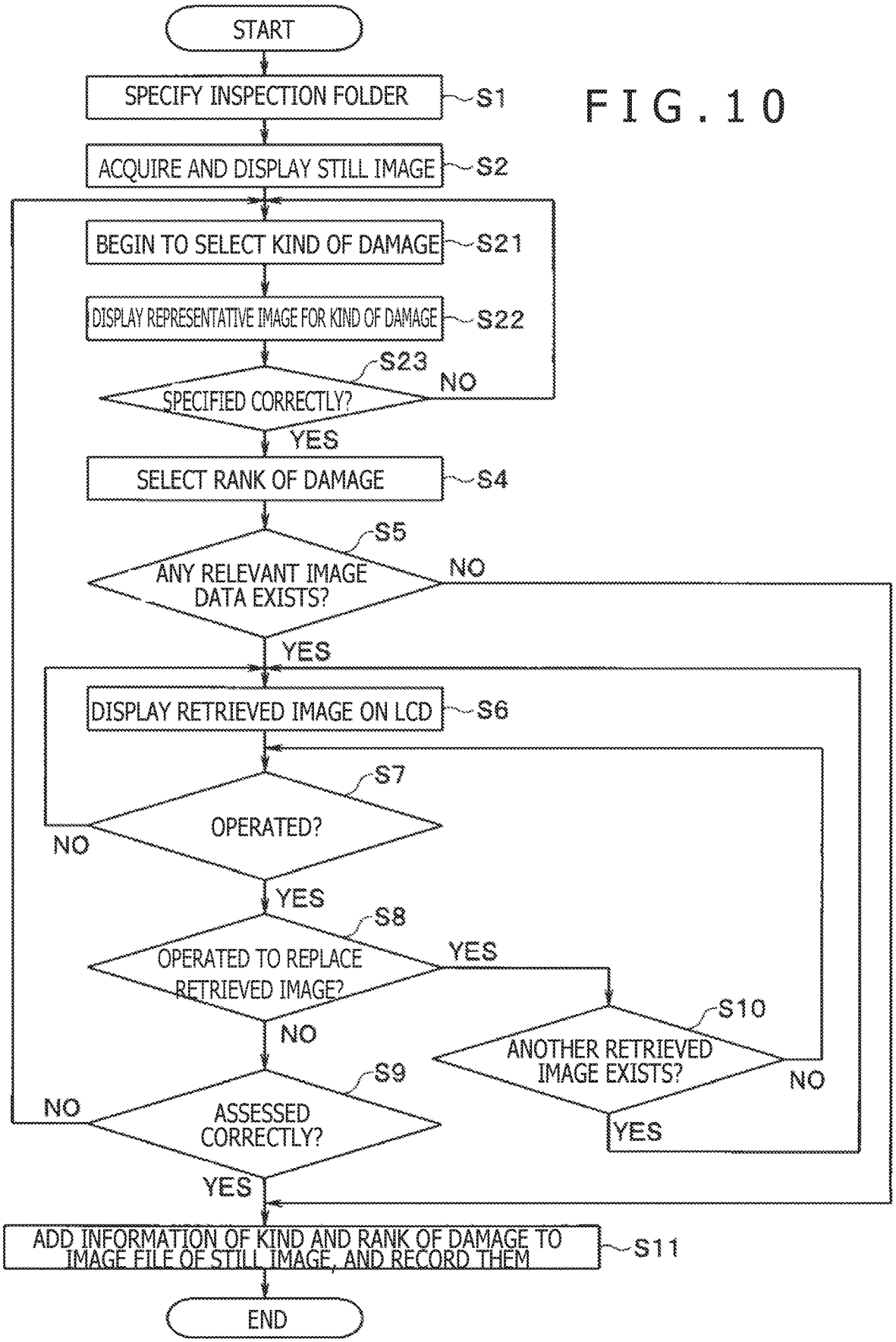
FIG. 10 is a flowchart illustrating operation of an endoscope device according to a second modification of the first embodiment.

FIG. 10 is a flowchart illustrating a second modification of the first embodiment. In FIG. 10, the same procedures as the corresponding ones in FIG. 4 are identified by the same reference symbols, and their description is not repeated herein again to avoid redundancy. In the first embodiment described hereinbefore, the instruction of the kind of damage by the user was received in step S3. In this second modification, a representative image is displayed to avoid any error in the instruction of the kind of damage. The representative image assists the selection of the kind of damage. In FIG. 10, the instruction of the kind of damage is enabled in steps S21 to S23 instead of step S3. If a still image of an inspection part is acquired and displayed in step S2, the CPU 21 controls the display unit 4 so as to display a menu for the selection of the kind of damage and receives user's operation for the selection of the kind of damage, both in step S21. If the user specifies the kind of damage, the CPU 21 (i) reads a representative image for the kind of damage, the representative image being recorded in the memory card 11, and (ii) controls the display unit 4 so as to display the representative image on the display screen 4*a* of the LCD 4 in step S22.

Figure 11:
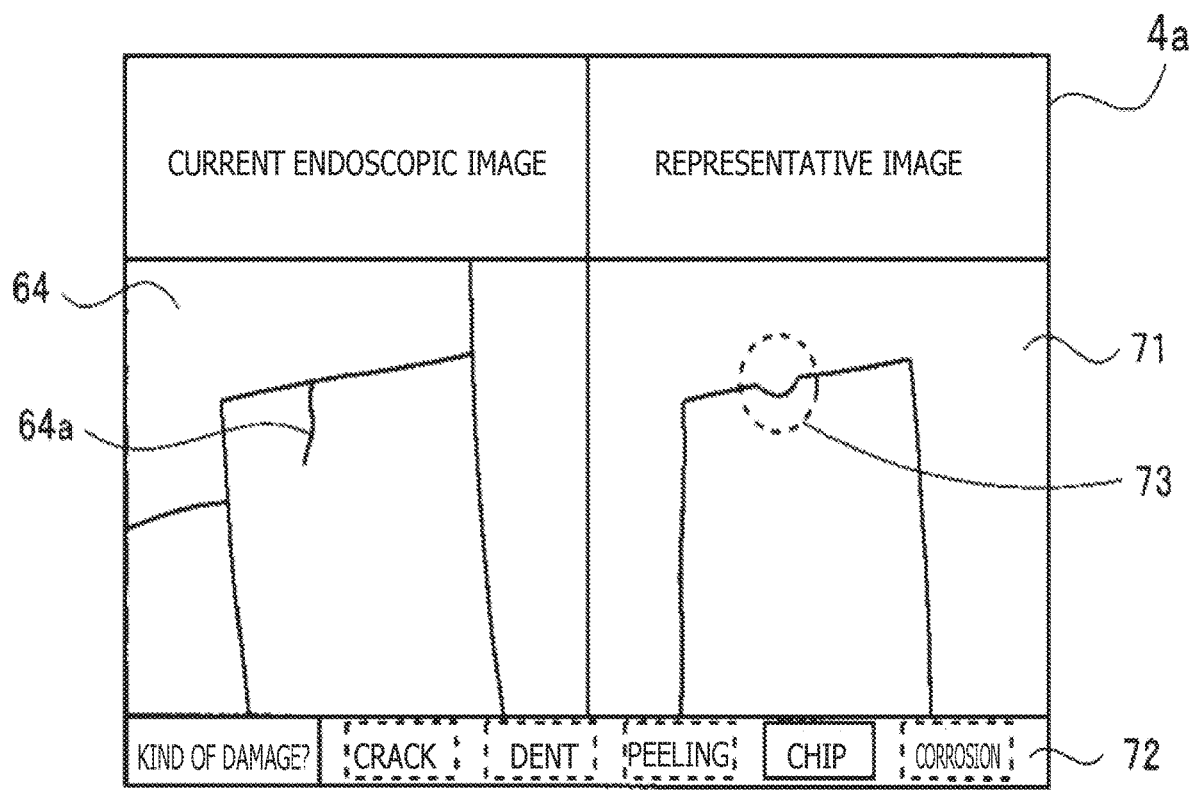
FIG. 11 is an illustration of an example of a display of a representative image in the operation of the endoscope device according to the second modification of the first embodiment.

FIG. 11 is an illustration of an example of a display of the representative image. In FIG. 11, the current endoscopic image 64 is displayed on the left side of the display screen 4*a*, and a representative image 71 is displayed on the right side of the display screen 4*a*. A menu 72 for the selection of the kind of damage is displayed at the lower end of the display screen 4*a*. Illustrated in the menu 72 is an example in which one of five kinds of damage including a crack, a dent, peeling, a chip and corrosion can be specified as the kind of damage. In the example of FIG. 11, user's selection is indicated by the solid line, and user's non-selection is indicated by the broken lines. In the example of FIG. 11, it is indicated that the user has selected "chip" as the kind of damage, and the representative image 71 of "chip" is displayed. In the representative image 71, a circle mark 73 that surrounds the damage to highlight the position of the damage is displayed. By comparing the endoscopic image and the representative image, the user is facilitated to determine whether his or her instruction as to the kind of damage is correct. In the example of FIG. 11, the crack 64*a* in the endoscopic image 64 and the "chip" surrounded by the circle mark 73 are clearly different in the kind of damage, so that the user can easily determine that his or her instruction of the kind of damage is wrong.

If it is determined, with reference to the damage in the endoscopic image and that in the representative image, that his or her instruction of the kind of damage is wrong, the user then performs an operation to specify the kind of damage again. The CPU 21 has already received user's operation as to whether the user's determination is correct in step 23. If it is determined in step S23 that there was user's operation whose instruction was indicated to be wrong, CPU 21 returns the processing to step 21, and receives user's operation for the instruction of the kind of damage. If it is determined that there was user's operation indicating the correctness of his or her determination, the CPU 21 (i) confirms the kind of damage specified by the user, (ii) allows the processing to proceed from step S23 to step S4, and then (iii) receives user's operation for the instruction of the rank of damage. Other operations, functions and effects are similar to those in FIG. 4. As the representative image of damage is displayed as described hereinbefore, the second modification can prevent the user from making an error in selecting the kind of damage. In the above description, as the display method of the representative image, the description was made about the example in which the endoscopic image is displayed on the left side and the representative image is displayed on the right side. However, similar to the case of the display of the endoscopic image and the assessment assist image, the individual displays hereinbefore and combinations thereof may also be adopted.

Figure 12:
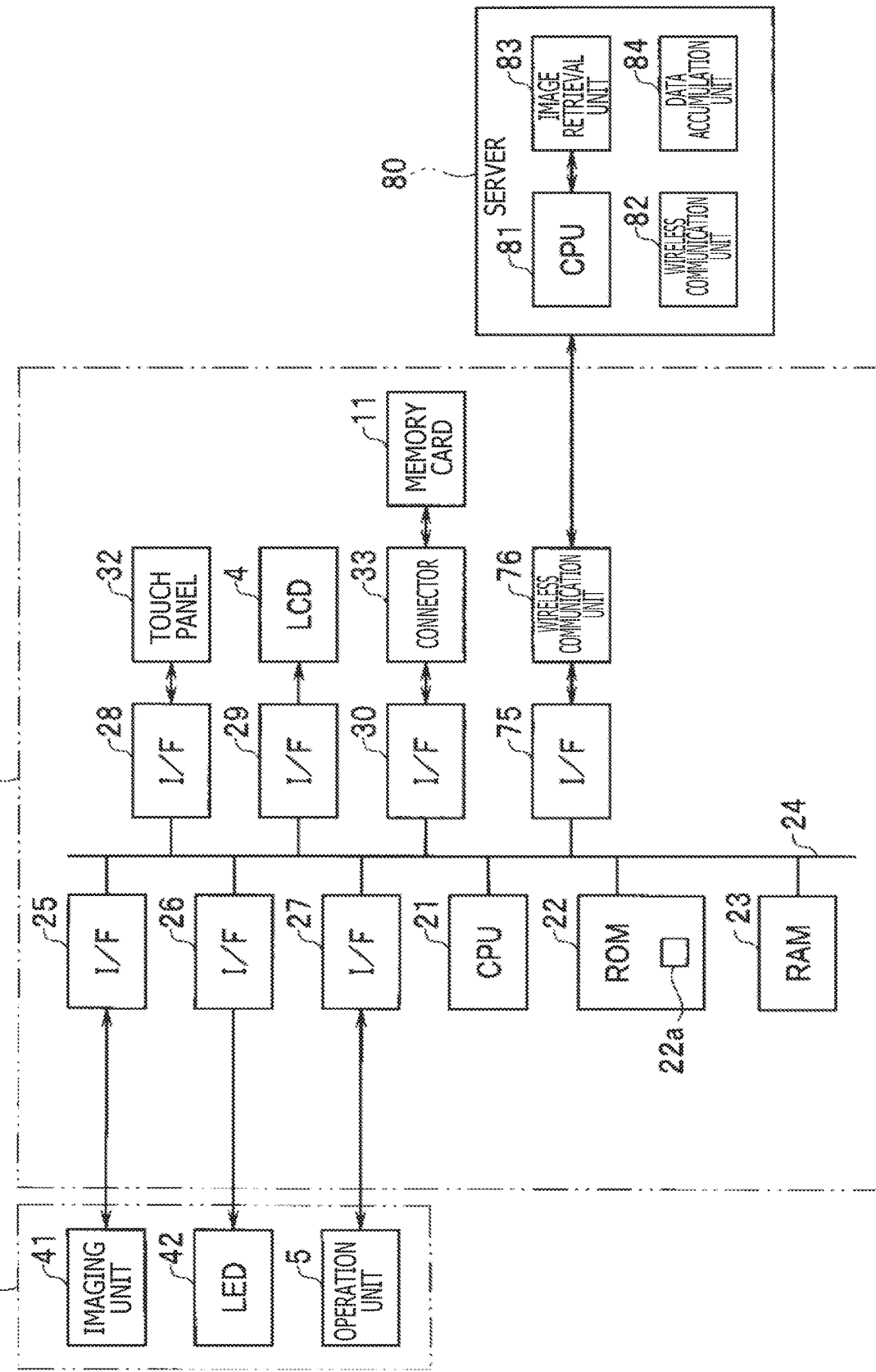
FIG. 12 is a block diagram illustrating an endoscope device according to a second embodiment of the present technology.

FIG. 12 is a block diagram illustrating a second embodiment of the technology disclosed herein. In FIG. 12, the same elements of configuration as the corresponding ones in FIG. 2 are identified by the same reference numerals, and their description is not repeated herein again to avoid redundancy. This second embodiment illustrates an example in which a recording medium in a server as an external device is adopted as a recording destination for image data. The recording medium stores endoscopic images, past images and reference images in their entirety or in part. If it is desired to record endoscopic images, past images and reference images in their entirety on the side of the server, the memory card fitted in the device console 2 or an unillustrated memory, which may be built in the device console 2, may be omitted. To transfer images from the server, a wireless transmission path or the like is adopted. The wireless transmission path or the like is slower in image transfer speed than the bus 24 in the device console 2. Therefore, an extended time is required to read past images, resulting possibly in a long inspection time because of the time needed for the transfer of the past images. This second embodiment is, therefore, intended to shorten the inspection time by estimating past images, for which a need is expected to arise, and transferring them beforehand from the server to the device console 2. To the device console 2, a wireless communication unit 76 is connected via an I/F 75 which is in turn connected to the bus 24. The wireless communication unit 76 can perform wireless communications with external devices. The I/F 75 supplies data from the CPU 21 to the wireless communication unit 76 and also supplies received data from the wireless communication unit 76 to the CPU 21.

A server 80 includes a CPU 81, which controls individual units in the server 80. The server 80 includes a wireless communication unit 82, which performs wireless communications with the wireless communication unit 76 of the device console 2 to perform data exchange. The CPU 81 delivers data, which the wireless communication unit 82 has received, to a data accumulation unit 84. The data accumulation unit 84 is configured of a hard disk, memory medium or the like. The CPU 81 controls the data accumulation unit 84 so as to store the data therein. The CPU 81 can also transmit data, which have been read from the data accumulation unit 84, to the wireless communication unit 76 of the device console 2 via the wireless communication unit 82. If a-data communication or instruction is generated from the CPU 21 of the device console 2 and the data communication or instruction is about an inspection folder as a recording destination for endoscopic images, the CPU 81 controls the data accumulation unit 84 based on the data communication or instruction. As a consequence, a predetermined inspection folder can be created in the data accumulation unit 84, and in addition, can also switch the recording destination folder for each endoscopic image based on user's operation. If an endoscopic image is transmitted from the device console 2, the CPU 81 delivers the endoscopic image to the data accumulation unit 84, and the CPU 81 controls the data accumulation unit 84 so as to record it in the inspection folder specified by the user. If a transfer request is generated from the device console 2 for assessment assist images, representative images and the like, the CPU 81 delivers information, which is required for the retrieval of these images, to an image retrieval unit 83, and instructs the retrieval of these images. The image retrieval unit 83 retrieves the images from the data accumulation unit 84 under control by the CPU 81, and delivers them to the CPU 81. The CPU 81 transfers the retrieved images to the device console 2 via the wireless communication unit 82.

In this second embodiment, the CPU 81 also predicts data, which are to be read from the data accumulation unit 84, based on data received via the wireless communication units 82 and 76. The CPU 81 allows the image retrieval unit 83 to retrieve the expected data from the data accumulation unit 84. Then the CPU 81 transfers the retrieved data to the device console 2. If an inspection folder as a recording destination for endoscopic images is specified from the CPU 21 of the device console 2, for example, the CPU 81 instructs the image retrieval unit 83 to read some of the image files of past images stored in the inspection folder. In this process, the read some image files each includes information (file mark) on a rank that indicates the occurrence of damage. If the image files specified by the image retrieval unit 83 are retrieved, the CPU 81 transfers the retrieved image files to the device console 2 via the wireless communication units 82 and 76. Here, the CPU 21 of the device console 2 controls to store the transferred image files, for example, in the RAM 23. Based on this configuration, upon displaying an endoscopic image and a past image, the CPU 21 can simply read and display one of the past images stored in the RAM 23. It is, therefore, possible to avoid an increase in inspection time that would otherwise occur due to the time needed for reading images from the server 80.

Figure 13:
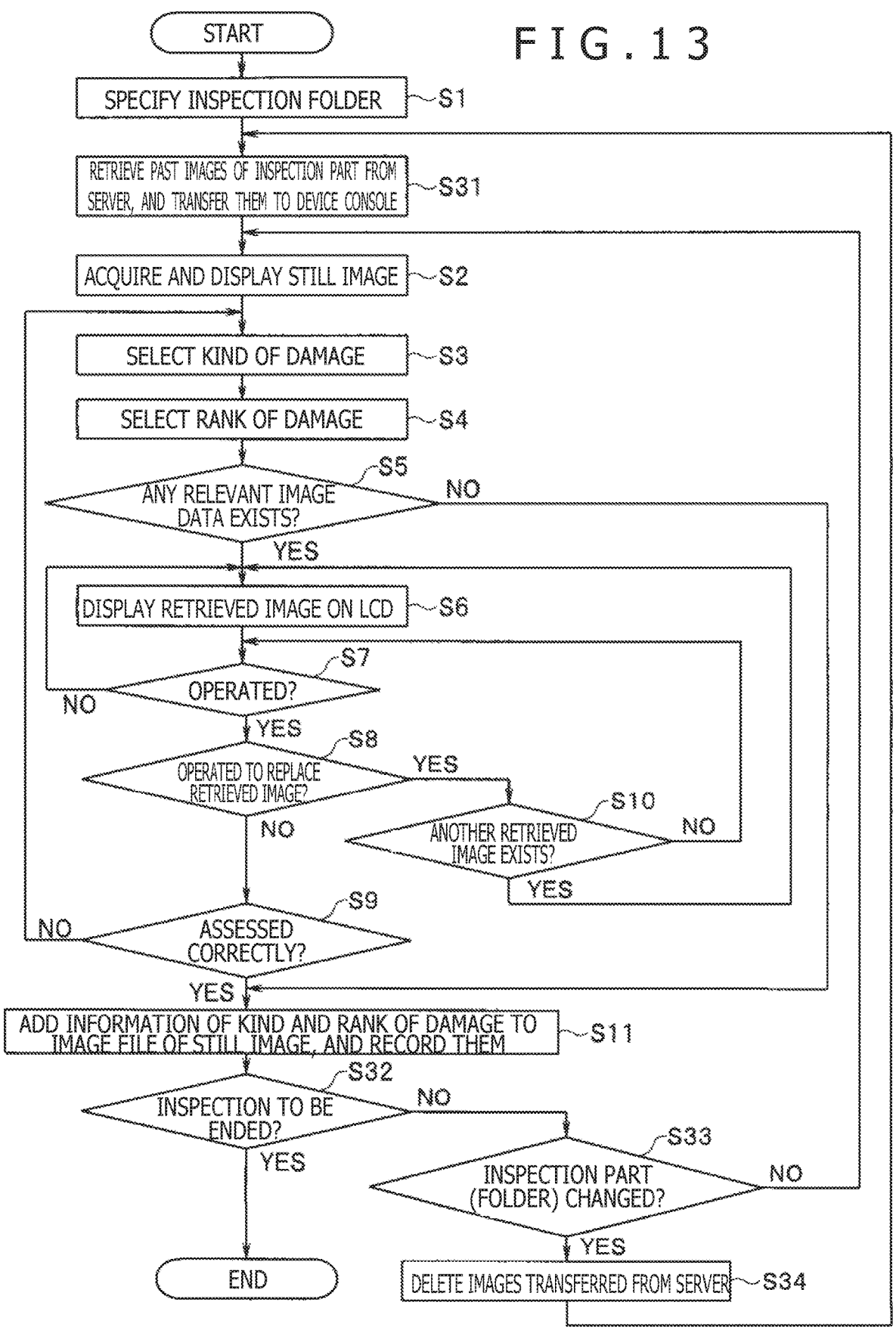
FIG. 13 is a flowchart for describing operation of the endoscope device of FIG. 12.

Referring to FIG. 13, a description will be made about operation of the second embodiment configured as described hereinbefore. FIG. 13 is a flowchart for describing operation of the second embodiment. In FIG. 13, the same procedures or steps as corresponding ones in FIG. 4 are identified by the same reference symbols, and their description is not repeated herein again to avoid redundancy. If the user specifies an inspection folder in step S1 of FIG. 13, the CPU 21 transmits information on the specified inspection folder to the server 80 via the wireless communication unit 76. If the information on the inspection folder is delivered via the wireless communication unit 82, the CPU 81 sets to record endoscopic images, which are to be subsequently transmitted from the device console 2, in the specified inspection folder.

In the second embodiment, before performing a retrieval of an assessment assist image by the CPU 21, the CPU 81 controls the image retrieval unit 83 to retrieve the images of inspection objects with damage or the like occurred thereon from past images stored in the specified inspection folder. The image retrieval unit 83 retrieves the images, for example, by relying upon the file marks included in their file names. The CPU 81 transfers the images, which have been retrieved by the image retrieval unit 83, to the device console 2 via the wireless communication unit 82 in step S31. The CPU 21 in the device console 2 controls the RAM 23 so as to store the transferred past images, for example, in the RAM 23.

While watching a live image and checking whether the tip portion 8 in the insert section 7 comes close to an inspection part, the user moves the tip portion 8 to look for the inspection part. If the tip portion 8 reaches an imaging position for the inspection part, then the user determines a part to be imaged and depresses the freeze button to perform imaging. The period from the user's operation to specify the inspection folder to the performance of imaging operation of the inspection part is relatively long, and during this period, the CPU 21 can transfer many of the past images to the device console 2.

If the user specifies the kind and rank of damage in steps S3 and S4, the CPU 21 retrieves one of the past images stored in the RAM 23 as an assessment assist image by using the kind and rank of damage as retrieval keys. The one past image matches the kind and rank of damage that the user specifies. The CPU 21 controls the LCD 4 so as to display it on the display screen 4a of the LCD 4. Among the past images recorded in the inspection folder in the data accumulation unit 84 of the server 80, those which have possibility of being displayed as assessment assist images have been transferred beforehand to the RAM 23. Therefore, one relevant assessment assist image can be displayed on the display screen 4a in a relatively short time from the instruction of the kind and rank of damage by the user.

In step S11, the CPU 21 performs processing to record an image file. Here, the CPU 21 transfers information, which is to be recorded, to the server 80 via the wireless communication unit 76. The CPU 81 of the server 80 delivers the image file of the endoscopic image to the data accumulation unit 84 to record it in the corresponding inspection folder.

If the processing of recording the image file is completed in step S11, the CPU 21 determines in the next step S32 whether an instruction to end the inspection is made. If the end of the inspection is instructed, the processing is ended. If the end of the inspection is not instructed, on the other hand, the CPU 21 determines in step S33 whether the instruction of an inspection folder corresponding to the inspection part is changed. If the inspection folder is not changed, the CPU 21 returns the processing to step S2, and repeats similar processing with respect to the next endoscopic image (still image). If the inspection folder is changed, the CPU 21 ( i ) allows the processing to proceed to step S34, (ii) deletes the endoscopic images (still images) transferred from the server 80 and stored in the RAM 23, and (iii) transfers information on an inspection folder, which has been newly specified by the user, to the CPU 81 of the server 80. Other operations, functions and effects are similar to those in FIG. 4. In the second embodiment, data such as image files are transferred from the device console to the external device, and are recorded in the external device. Here, if an inspection folder is specified, for example, some of the past images are retrieved and transferred beforehand to the device console. Said some past images are stored in the specified inspection folder in the external device. Said some past images each is of an inspection object having an abnormality such as damage. As a consequence, the device console can perform the display of an assessment assist image in a relatively short time, and therefore can shorten the inspection time.

The respective "units" in this specification are conceptual elements corresponding to the individual functions of the embodiments, and do not necessarily correspond to any specific hardware or software routine in a one-to-one relationship. In each embodiment described above, the embodiment is described assuming imaginary circuit blocks (units) having the individual functions. Further, the steps of the respective procedures in the embodiments may be performed by changing the order of their execution, by performing plural ones of them at the same time, or in a different order every time they are performed. Furthermore, the steps of the respective procedures in the embodiments may be realized in their entirety or in part by hardware, unless contrary to the nature thereof.

The disclosed technology should not be limited to the aforementioned embodiments, and various changes, modifications and the like are feasible within a scope not altering the spirit of the present technology.

It should be understood by those skilled in the art that various modifications, combinations, sub-combinations and alterations may occur depending on design requirements and other factors insofar as they are within the scope of the appended claims or the equivalents thereof.

While various embodiments of the disclosed technology have been described above, it should be understood that they have been presented by way of example only, and not of limitation. Likewise, the various diagrams may depict an example schematic or other configuration for the disclosed technology, which is done to aid in understanding the features and functionality that can be included in the disclosed technology. The disclosed technology is not restricted to the illustrated example schematic or configurations, but the desired features can be implemented using a variety of alternative illustrations and configurations. Indeed, it will be apparent to one of skill in the art how alternative functional, logical or physical locations and configurations can be implemented to implement the desired features of the technology disclosed herein.

Although the disclosed technology is described above in terms of various exemplary embodiments and implementations, it should be understood that the various features, aspects and functionality described in one or more of the individual embodiments are not limited in their applicability to the particular embodiment with which they are described, but instead can be applied, alone or in various combinations, to one or more of the other embodiments of the disclosed technology, whether or not such embodiments are described and whether or not such features are presented as being a part of a described embodiment. Thus, the breadth and scope of the technology disclosed herein should not be limited by any of the above-described exemplary embodiments.

Terms and phrases used in this document, and variations thereof, unless otherwise expressly stated, should be construed as open ended as opposed to limiting. As examples of the foregoing: the term "including" should be read as meaning "including, without limitation" or the like; the term "example" is used to provide exemplary instances of the item in discussion, not an exhaustive or limiting list thereof; the terms "a" or "an" should be read as meaning "at least one," "one or more" or the like; and adjectives such as "conventional," "traditional," "normal," "standard," "known" and terms of similar meaning should not be construed as limiting the item described to a given time period or to an item available as of a given time, but instead should be read to encompass conventional, traditional, normal, or standard technologies that may be available or known now or at any time in the future. Likewise, where this document refers to technologies that would be apparent or known to one of ordinary skill in the art, such technologies encompass those apparent or known to the skilled artisan now or at any time in the future.

The presence of broadening words and phrases such as "one or more," "at least," "but not limited to" or other like phrases in some instances shall not be read to mean that the narrower case is intended or required in instances where such broadening phrases may be absent. Additionally, the various embodiments set forth herein are described in terms of exemplary schematics, block diagrams, and other illustrations. As will become apparent to one of ordinary skill in the art after reading this document, the illustrated embodiments and their various alternatives can be implemented without confinement to the illustrated examples. For example, block diagrams and their accompanying description should not be construed as mandating a particular configuration.

What is claimed is:

1. An endoscope device comprising:
a processor configured to:
receive, through an input device, an assessment on an endoscopic image of an object as captured by an image sensor;
retrieve, based on the assessment, one assessment assist image of a plurality of assessment assist images stored in a data storage,
wherein the one assessment assist image retrieved is a past endoscopic image of the object captured by the image sensor, a past endoscopic image of an object of a same type of the object as captured by the image sensor, or a reference image; and
control a display to display the one assessment assist image retrieved along with the endoscopic image,
wherein the processor is configured to preferentially retrieve, based on the assessment, the one assessment assist image of the plurality of assessment assist images in an order of:
the past endoscopic image of the object captured by the image sensor;
the past endoscopic image of the object of the same type of the object as captured by the image sensor; and
the reference image, and
wherein the processor is configured to control the display to indicate the one assessment assist image under display is one of:
the past endoscopic image of the object captured by the image sensor;
the past endoscopic image of the object of the same type of the object as captured by the image sensor; and
the reference image.

2. The endoscope device of claim 1,
wherein the processor is configured to:
receive, through the input device, information on an inspection part of the object captured in the endoscopic image of the object; and
retrieve, based on the assessment and the information on the inspection part of the object captured in the endoscope image of the object, the one assessment assist image of the plurality of assessment assist images stored in the data storage.

3. The endoscope device of claim 1,
wherein the processor is configured to:
receive, through the input device, a corrected assessment on the endoscopic image of the object;
re-retrieve, based on the corrected assessment, another assessment assist image of the plurality of assessment assist images stored in the data storage; and
control the display to display the another assessment assist image retrieved along with the endoscopic image.

4. The endoscope device of claim 1,
wherein the processor is configured to:
receive, through the input device, an operation command to confirm the assessment; and
responsive to the operation command to confirm the assessment, control the data storage to record the assessment along with the endoscopic image.

5. The endoscope device of claim 4,
wherein the processor is configured to:
receive, through the input device, an instruction to specify an inspection folder in which the endoscopic image is to be recorded; and
control the data storage to store, in the inspection folder specified by the instruction, the assessment along with the endoscopic image.

6. The endoscope device of claim 1,
wherein the processor is configured to:
receive, through the input device, an operation command to switch an assessment assist image to be displayed; and
responsive to the operation command to switch the assessment assist image to be displayed:
retrieve another assessment assist image of the plurality of assessment assist images; and
control the display to switch from display of the one assessment assist image retrieved to display the another assessment assist image retrieved.

7. The endoscope device of claim 1,
wherein the assessment represents a kind, rank or both the kind and the rank of damage of the object.

8. The endoscope device of claim 1,
wherein the one assessment assist image retrieved is the past endoscopic image of the object as captured by the image sensor, information on a kind and rank of damage of the object as captured by the image sensor being added to the past endoscopic image, the past endoscopic image of an object of the same type of the object as captured by the image sensor, information on a kind and rank of damage of the object of the same type being added to the past endoscopic image; or the reference image prepared as a reference for a kind and rank of damage.

9. The endoscope device of claim 1,
wherein the processor is configured to:
control the data storage to store the plurality of assessment assist images such that each of the plurality of assessment assist images has a mark that indicates a position of an abnormal part added;
set a setting for the mark to be visible or invisible upon display of the one assessment assist image retrieved; and
control the display to display the one assessment assist image retrieved with the mark being visible or invisible based on the setting.

10. The endoscope device of claim 1,
wherein each of the plurality of assessment assist images represents a different kind, rank or both the kind and the rank of damage of the object, and
wherein the processor is configured to retrieve the one assessment assist image of the plurality of assessment assist images having the kind, the rank or both the kind and the rank of damage corresponding to the assessment received.

11. An endoscope system comprising:
an endoscope comprising an image sensor;
an input device;
a server configured to store a plurality of assessment assist images; and
a processor configured to:
receive, through the input device, an assessment on an endoscopic image of an object as captured by the image sensor of the endoscope;
retrieve, based on the assessment, one assessment assist image of the plurality of assessment assist images stored in the server;
wherein the one assessment assist image retrieved is a past endoscopic image of the object captured by the image sensor, a past endoscopic image of an object of a same type of the object as captured by the image sensor, or a reference image; and control a display to display the one assessment assist image retrieved along with the endoscopic image, wherein the processor is configured to preferentially retrieve, based on the assessment, the one assessment assist image of the plurality of assessment assist images in an order of:

the past endoscopic image of the object captured by the image sensor;

the past endoscopic image of the object of the same type of the object as captured by the image sensor; and the reference image, and wherein the processor is configured to control the display to indicate the one assessment assist image under display is one of:

the past endoscopic image of the object captured by the image sensor;

the past endoscopic image of the object of the same type of the object as captured by the image sensor; and the reference image.

12. The endoscope system of claim 11, wherein the endoscope comprises a memory, and wherein the server is configured to transfer the plurality of assessment assist images, which have been stored in the server, to the memory of the endoscope for storage in the memory.

13. The endoscope system of claim 12, wherein the processor is configured to retrieve, based on the assessment, the one assessment assist image of the plurality of assessment assist images which have been transferred from the server and stored in the memory.

14. The endoscope system of claim 12, wherein the processor is configured to delete the plurality of assessment assist images, which have been stored in the memory from before, when storing new assessment assist images in the memory.

15. An inspection method of an endoscope system, the inspection method comprising:

receiving, through an input device, an assessment on an endoscopic image of an object as captured by an image sensor;

retrieving, based on the assessment, one assessment assist image of a plurality of assessment assist images stored in a data storage, wherein the one assessment assist image retrieved is a past endoscopic image of the object captured by the image sensor, a past endoscopic image of an object of a same type of the object as captured by the image sensor, or a reference image; and controlling a display to display the one assessment assist image retrieved along with the endoscopic image, wherein retrieving the one assessment assist image comprises preferentially retrieving, based on the assessment, the one assessment assist image of the plurality of assessment assist images in an order of:

the past endoscopic image of the object captured by the image sensor;

the past endoscopic image of the object of the same type of the object as captured by the image sensor; and the reference image, and wherein controlling the display to display the one assessment assist image retrieved comprises controlling the display to indicate the one assessment assist image under display is one of:

the past endoscopic image of the object captured by the image sensor;

the past endoscopic image of the object of the same type of the object as captured by the image sensor; and the reference image.

* * * * *